US007223770B2

(12) United States Patent
Zhang et al.

(10) Patent No.: US 7,223,770 B2
(45) Date of Patent: May 29, 2007

(54) TOCOPHEROL-MODIFIED THERAPEUTIC DRUG COMPOUNDS

(75) Inventors: Yuehua Zhang, Mill Creek, WA (US); Lynn C. Gold, Seattle, WA (US)

(73) Assignee: Sonus Pharmaceuticals, Inc., Bothell, WA (US)

( * ) Notice: Subject to any disclaimer, the term of this patent is extended or adjusted under 35 U.S.C. 154(b) by 43 days.

(21) Appl. No.: 10/978,222

(22) Filed: Oct. 29, 2004

(65) Prior Publication Data
US 2005/0096340 A1 May 5, 2005

Related U.S. Application Data

(60) Provisional application No. 60/621,655, filed on Oct. 26, 2004, provisional application No. 60/558,762, filed on Apr. 1, 2004, provisional application No. 60/556,137, filed on Mar. 24, 2004, provisional application No. 60/515,364, filed on Oct. 29, 2003.

(51) Int. Cl.
A61K 31/4745 (2006.01)
C07D 45/02 (2006.01)

(52) U.S. Cl. .................. 514/283; 546/48
(58) Field of Classification Search ........ 514/283, 514/528; 546/48
See application file for complete search history.

(56) References Cited

U.S. PATENT DOCUMENTS

| 4,665,204 | A | 5/1987 | Wirth |
| 5,234,695 | A | 8/1993 | Hobbs et al. |
| 5,606,080 | A | 2/1997 | Ogata et al. |
| 5,610,180 | A | 3/1997 | Fariss |
| 5,795,909 | A | 8/1998 | Shashoua et al. |
| 5,858,398 | A | 1/1999 | Cho |
| 5,891,469 | A | 4/1999 | Amselem |
| 5,917,060 | A | 6/1999 | Rosenau et al. |
| 5,945,409 | A | 8/1999 | Crandall |
| 6,045,826 | A | 4/2000 | Borowy-Borowski et al. |
| 6,191,172 | B1 | 2/2001 | Borowy-Borowski et al. |
| 6,319,943 | B1 | 11/2001 | Joshi et al. |
| 6,387,882 | B1 | 5/2002 | Ogata et al. |
| 6,417,223 | B1 | 7/2002 | Sanders et al. |
| 6,458,373 | B1 | 10/2002 | Lambert et al. |
| 6,479,540 | B1 * | 11/2002 | Constantinides et al. ... 514/458 |
| 6,545,125 | B1 | 4/2003 | Fujii |
| 6,576,636 | B2 | 6/2003 | Webb et al. |
| 6,660,286 | B1 * | 12/2003 | Lambert et al. ............ 424/405 |
| 6,683,194 | B2 | 1/2004 | Zhang et al. |
| 6,727,280 | B2 | 4/2004 | Palepu et al. |
| 6,858,227 | B1 * | 2/2005 | Lal et al. .................... 424/450 |
| 2002/0103254 | A1 * | 8/2002 | Joshi-Hangal et al. ...... 514/449 |

FOREIGN PATENT DOCUMENTS

| DE | 4423915 A1 | 1/1996 |
| EP | 0 008 573 A1 | 3/1980 |
| GB | 1 395 994 A | 5/1975 |
| GB | 1 409 612 A | 10/1975 |
| WO | WO 95/11039 A1 | 4/1995 |
| WO | WO 95/31217 A1 | 11/1995 |
| WO | WO 97/44026 A1 | 11/1997 |
| WO | WO 97/44336 A1 | 11/1997 |
| WO | WO 99/04787 A1 | 2/1999 |
| WO | WO 00/71163 A1 | 11/2000 |
| WO | WO 02/076970 A2 | 10/2002 |
| WO | WO 02/083067 A2 | 10/2002 |

OTHER PUBLICATIONS

Nielsen, et al., "The effect of alpha-tocopherol on the in vitro solubilisation of lipophilic drugs" Internation J. of Pharmaceutics 222, (2001) 217-224.*
Constantinides, et al., "Tocol emulsions for drug solubilization and parenteral delivery", Advanced Drug Delivery Reviews 56, (2204), 1243-1255.*
Cancer Classification (available at: http://training.seer.cancer.gov/module_cancer_disease/unit3_categories2_by_histology.html).*
Grever et al., The National Cancer Institute: Cancer Drug Discovery and Development Program, Seminars in Oncology, 19:6 622-638 (1992).*
product description for HTB-177 (available at http://www.atcc.org/common/catalog/numSearch/numResults.cfm?atccNum=HTB-177).*
ATCC "product description Cell culture HTB-161" (2007).*
Clontech laboratories, Inc. "Product description: cancer cell lines" (2007).*
Edeas, M.A., et al., "Protective Effects of the Lipophilic Redox Conjugate Tocopheryl Succinyl-Ethyl Ferulate on HIV Replication," FEBS Letters 418:15-18, 1997.
Lalloo, A.K., et al., "Membrane Transport of Camptothecin: Facilitation by Human P-Glycoprotein (ABCB1) and Multidrug Resistance Protein 2 (ABCC2)," Biomedcentral.com, <http://www/biomedcentral.com/1741-7015/2/16> [retrieved Oct. 28, 2004]; also available BMC Medicine 2:16, 2004.
Li, C., et al., "Antitumor Activity of Poly(L-Glutamic Acid)-Paclitaxel on Syngeneic and Xenografted Tumors," Clinical Cancer Research 5:891-897, Apr. 1999.
Qasem, J.G., et al., Kinetics of Paclitaxel 2'-N-methylpyridinium Mesylate Decomposition, AAPS PharmSciTech 4(2):1-8; also available www.pharmscitech.org.
Rigas, J.R., "Taxane-Platinum Combinations in Advanced Non-Small Cell Lung Cancer: A Review," The Oncologist, <http://thoncologist.alphamedpress.org/cgi/content/full/9/suppl_2/16> [retrieved Oct. 28, 2004]; also available The Oncologist 9, Suppl. 2, 16-23, Jun. 2, 2004.

(Continued)

Primary Examiner—Celia Chang
(74) Attorney, Agent, or Firm—Christensen O'Connor Johnson Kindness PLLC

(57) ABSTRACT

Tocopherol-modified therapeutic drug compounds; emulsion, microemulsion, and micelle formulations that include the compounds; methods for making the compounds and formulations; methods for administering the compounds and formulations; and methods for treating conditions using the compounds and formulations.

14 Claims, 17 Drawing Sheets

OTHER PUBLICATIONS

Ansel, S.M., et al., Synthesis and Formulation of a Lipophilic Prodrug of Paclitaxel for Liposomal Delivery, *Abstracts of Papers American Chemical Society 212*(1-2), p. MEDI 48, and 212th American Chemical Society National Meeting, Orlando, Florida, Aug. 25-29, 1996 (abstract only).

Dallavalle, S., et al., "Perspectives in Camptothecin Development," *Expert Opinion on Therapeutic Patents 12*(6):837-844, 2002.

Liu, X., et al., "A Versatile Prodrug Approach for Liposomal Core-Loading of Water-Insoluble Camptothecin Anticancer Drugs," *J. Am. Chem. Soc. 124*(26):7650-7651, 2002.

Lundberg, B.B., et al., "A Lipophilic Paclitaxel Derivative Incorporated in a Lipid Emulsion for Parenteral Administration," *Journal of Controlled Release 86*(1):93-100, Jan. 9, 2003.

* cited by examiner

TOCOPHEROL-MODIFIED THERAPEUTIC DRUG COMPOUNDS

CROSS-REFERENCES TO RELATED APPLICATIONS

This application claims the benefit of U.S. Provisional Application No. 60/621,655, filed Oct. 26, 2004, entitled TOCOPHEROL-MODIFIED THERAPEUTIC DRUG COMPOUNDS, and claims the benefit of U.S. Provisional Application No. 60/515,364, filed Oct. 29, 2003, U.S. Provisional Application No. 60/556,137, filed Mar. 24, 2004, and U.S. Provisional Application No. 60/558,762, filed Apr. 1, 2004, incorporated by reference herein in their entirety.

FIELD OF THE INVENTION

The present invention relates to new therapeutic drugs; compositions that include the new therapeutic drugs; and methods for administering and using the new therapeutic drugs and compositions.

BACKGROUND OF THE INVENTION

The ability to administer biologically effective drugs that are poorly soluble in biocompatible solvents to mammals has been a major hurdle in the realm of pharmaceutical and medicinal chemistry. In particular, difficulties arise when an active drug is either insoluble in water or unstable in other biocompatible solvents.

One way to solubilize medicinal agents is to chemically modify them or conjugate them to another molecule to alter the solubility profile in a particular solvent. Conjugates of active drugs, often referred to as prodrugs, include chemical derivatives of biologically-active parent compounds that are converted into the parent compounds in vivo. The release of the active parent drug from the prodrug conjugate may occur as the result of processes such as hydrolysis or enzymatic cleavage. The rate of release is influenced by several factors, including the type of chemical bond joining the active parent drug to the conjugate moiety.

Incorporating a water-soluble moiety (e.g., polyethylene glycol, polyglutamate, or polymer) to increase solubility and circulation life of a drug has been investigated by others. The use of fatty acids to conjugate to active drugs for purposes of tumor targeting has also been investigated as a means of improving therapeutic index.

Many potent drugs, such as camptothecin and its analogues (e.g., 10-hydroxycamptothecin and 7-ethyl-10-hydroxycamptothecin), taxanes (e.g., paclitaxel, docetaxel), candesartan, amphotericin B, azathioprine, cyclosporine, entacapone, danazol, eletriptan, and bosentan, to name a few, are poorly soluble or have poor cell permeability. Solubility problems of potential therapeutic agents are common and often cause delays in drug development. Several technologies have been developed to facilitate the delivery of poorly soluble and insoluble compounds to patients. Examples of technologies specifically designed to solve solubility problems include complexing agents, nanoparticles, microemulsions, solubility enhancing formulations, prodrugs, and novel polymer systems.

Paclitaxel (see structure below), a natural product found in the inner bark of the Pacific Yew tree, is an example of an important chemotherapeutic agent with wide spectrum of activity against solid tumors, primarily breast, ovarian, colon and non-small cell lung cancer.

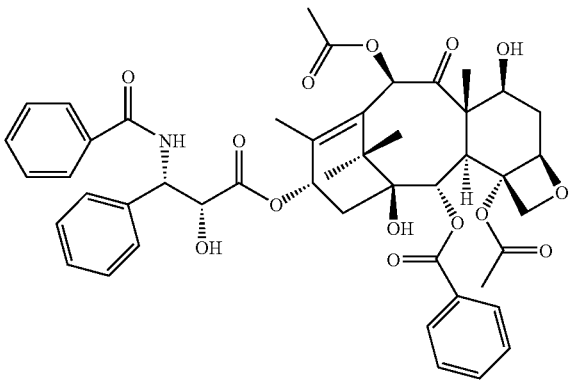

Paclitaxel exerts its antitumor activity by binding to tubulin and stabilizing microtubules and thus blocking cell mitosis. However, paclitaxel, like many other potent biologically active molecules, has very limited aqueous solubility.

Camptothecin (CPT) (see structure below) is another example of a poorly soluble and difficult to formulate anti-cancer drug.

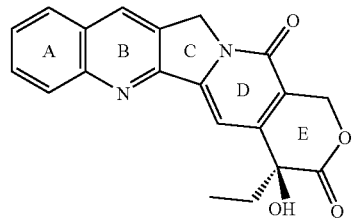

CPT is a quinoline-based alkaloid found in the bark of the Chinese camptotheca tree and the Asian nothapodytes tree. CPT includes four planar rings (ABCD) and one boat conformational ring (E). CPT has been found to have a broad spectrum of antitumor activity, especially in human solid tumors. However, the lactone (ring E) of camptothecin and its derivatives is quite labile in alkaline condition and physiological pH. The opening of this ring to form an acid salt or carboxylate species results in significant loss of anticancer activities. Efforts have been made since the early 1960s, when CPT was discovered by Wall and Wani, to improve upon the anti-cancer activities formulation of camptothecin has been developed to date because of its poor solubility in both water and organic solvents. However, water-soluble analogues of camptothecin, irinotecan hydrochloride (CAMPTOSAR) and topotecan hydrochloride (HYCAMPTIN), have been developed and are the only camptothecin analogs currently approved by the Food and Drug Administration.

Recently, a vitamin E (α-tocopherol)-based emulsion formulation technology for paclitaxel drug delivery has been developed. In the formulation, paclitaxel is solubilized in α-tocopherol and formulated as an oil-in-water emulsion. However, while paclitaxel is soluble in α-tocopherol, the solubility of other active moieties (including camptothecin and other taxanes) in α-tocopherol is limited. Therefore, there continues to be a need for new methods, which are both safe and efficacious, of solubilizing and delivering poorly soluble active drug molecules.

SUMMARY OF THE INVENTION

In one aspect, the present invention provides therapeutic drug compounds that have been modified to increase their lipophilicity. The compounds of the invention include a one or more therapeutic drug moieties and one or more lipophilic moieties. The therapeutic drug moiety is covalently coupled to the lipophilic moiety either directly or by a linker moiety. Methods for making the modified therapeutic drugs are also provided.

In another aspect of the invention, compositions that include the compounds of the invention are provided. In one embodiment, the composition includes a compound of the invention, optionally one or more other therapeutic agents, and a lipophilic medium. Methods for making the compositions are also provided.

In a further aspect, the invention provides emulsion and micelle formulations that include a compound of the invention. The emulsion formulation include an oil phase and an aqueous phase. The oil phase includes a compound of the invention and a lipophilic medium. The emulsion may be an oil-in-water emulsion or a water-in-oil emulsion. The micelle formulation includes a compound of the invention and an aqueous phase. Methods for making the emulsion and micelle formulations are also provided.

In other aspects, methods for administering the compounds of the invention to a subject in need thereof, and methods for treating a condition treatable by administration of a compound of the invention are also provided.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 14B, SN2310); FIG. 15B, HT-29).

DETAILED DESCRIPTION OF THE PREFERRED EMBODIMENT

Figure 1:
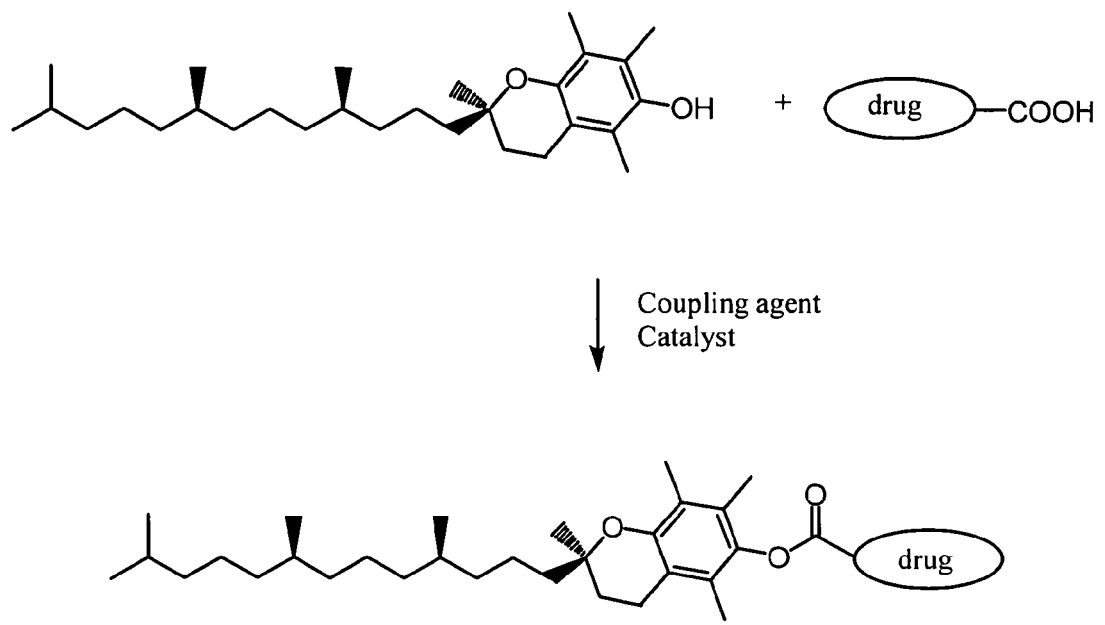
FIG. 1 schematically illustrates reaction of d-α-tocopherol and a therapeutic drug containing a carboxyl group to provide a tocopherol-modified therapeutic drug compound.

In one aspect, the present invention provides therapeutic drug compounds that have been modified to increase their lipophilicity. The compounds of the invention are modified therapeutic drugs. The compounds of the invention include a therapeutic drug moiety and a lipophilic moiety.

In some embodiments, the compounds of the invention include more than one therapeutic drug moiety. In some embodiments, the compounds of the invention include more than one lipophilic moiety. In other embodiments, the compounds of the invention include more than one therapeutic drug moiety and more than one lipophilic moiety.

In some embodiments, the therapeutic drug moiety is covalently coupled to the lipophilic moiety through a linker moiety. In other embodiments, the therapeutic drug moiety is directly covalently coupled to the lipophilic moiety without a linker moiety.

In one embodiment, the lipophilic moiety is a tocopherol moiety, and the compound is a tocopherol-modified therapeutic drug compound. The tocopherol-modified therapeutic drug compound (or "tocopherolated" therapeutic drug compound) has one or more tocopherol moieties covalently coupled to a therapeutic drug moiety or a tocopherol moiety covalently coupled to one or more therapeutic drug moieties. As noted above, the tocopherol moiety is covalently coupled to the therapeutic drug moiety either directly or through a linker moiety.

In one embodiment, the tocopherol-modified therapeutic drug compounds of the invention can be represented by the general formula (1):

$$(T-L)_n(T)_mD \qquad (1)$$

wherein T is a tocopherol moiety (i.e., a representative lipophilic moiety); L is a linker moiety; n is 0, 1, 2, or 3; m is 0, 1, 2, or 3; n+m is 1, 2, or 3; and D is a therapeutic drug moiety. In this embodiment, the compound includes n T-L moieties (i.e., tocopherol-linker moieties) and m tocopherol moieties, with the proviso that n+m is 1, 2, or 3. Each T-L moiety includes a tocopherol moiety covalently coupled to a linker moiety. Each of the n T-L moieties is covalently coupled to the therapeutic drug moiety through the T-L moiety's linker moiety. In this embodiment, each of the m tocopherol moieties is directly covalently coupled to the therapeutic drug moiety without a linker moiety.

Representative compounds having formula (1) include those in which n is 0 and m is 1, 2, or 3. These compounds have the general formula:

$$T_mD \qquad (2)$$

In this embodiment, one, two, or three tocopherol moieties are directly covalently coupled to the therapeutic drug moiety.

Representative compounds having formula (1) include those in which m is 0 and n is 1, 2, or 3. These compounds have the general formula:

$$(T-L)_nD \qquad (3)$$

In this embodiment, one, two, or three T-L moieties are covalently coupled to the therapeutic drug moiety through the T-L moiety's linker moiety.

Representative compounds having formula (1) include those in which m is 1 or 2, and n is 1 or 2. These compounds have the general formulae:

$$(T-L)(T)D \qquad (4)$$

$$(T-L)(T)_2D \qquad (5)$$

$$(T-L)_2(T)D \qquad (6)$$

In these embodiments, the compounds of the invention have tocopherol moieties that are directly covalently coupled to the therapeutic drug moiety without a linker and tocopherol moieties that are covalently coupled to the therapeutic drug moiety through a linker (i.e., the T-L moieties).

The compounds of the invention described above include one therapeutic drug moiety and one or more lipophilic moieties (e.g., tocopherol moieties). In other embodiments, the compounds of the invention include more than one therapeutic drug moiety. In one embodiment, the compounds include two therapeutic drug moieties. In another embodiment, the compounds include three therapeutic drug moieties. For compounds that include more than one therapeutic drug moiety, the therapeutic drug moieties a can be the same or different.

For compounds that include more than one therapeutic drug moiety, the therapeutic drug moieties can be incorporated into the compound in any suitable way. In some embodiments, the therapeutic drug moieties can be directly covalently coupled (e.g., the compound includes a -D-D- or -D-D moiety). In other embodiments, the therapeutic drug moieties are separated in the compound by a linker moiety (e.g., the compound includes a -D-L-D- or -D-L-D moiety), a lipophilic moiety (e.g., the compound includes a -D-T-D- or -D-T-D moiety), or a lipophilic-linker moiety (e.g., the compound includes a -D-T-L-D-, -D-T-L-D, or -D-L-T-D moiety; or a -D-L-T-L-D- or -D-L-T-L-D moiety).

Representative compounds including two or three therapeutic drug moieties have the general formula:

$$(T-L)(D)_p \qquad (7)$$

wherein p is 2 or 3. In this embodiment, the two or three therapeutic drug moieties are covalently coupled to the linker moiety. In this instance, the linker includes multiple sites for the attachment of the therapeutic drug compound (or modified therapeutic drug compound). As is clear from formula (7), the linker moiety is also covalently coupled to the lipophilic moiety (e.g., tocopherol moiety). As noted above, compounds of the invention including more than one therapeutic drug moiety can have formulae other than shown above in formula (7). For example, such a compound can include more than one (e.g., two or three) lipophilic (e.g., tocopherol) moieties.

The compounds of the invention include one or more lipophilic moieties and one or more therapeutic drug moieties that are either directly covalently linked or covalently linked through linker moieties.

As used herein, the term "lipophilic moiety" refers to a chemical moiety having lipophilic or hydrophobic characteristics and that increases the solubility of a therapeutic drug compound in a lipophilic solvent or environment when covalently coupled to the therapeutic drug compound to provide a compound of the invention. A description of representative lipophilic moieties useful in making the compounds of the invention is provided below.

As used herein, the term "therapeutic drug moiety" refers to a chemical moiety derived from a therapeutic drug compound. A description of representative therapeutic drug compounds useful in making the compounds of the invention is provided below.

As used herein, the term "linker moiety" refers to an atom or a group of atoms that covalently link, for example, a lipophilic moiety to a therapeutic drug moiety. A description of representative linkers useful in making the compounds of the invention is provided below.

Lipophilic Modification of Therapeutic Drug Compounds. A therapeutic drug compound may have one or more suitable functional groups, or may be modified to include one or more suitable functional groups for covalent coupling to a lipophilic moiety. Suitable functional groups include, for example, the following groups: hydroxyl group (—OH), amino group (primary amino group, —NH$_2$, or secondary amino group, —NHR$_1$, where R$_1$ is independently selected from H, C$_{1-6}$ n-alkyl, C$_{3-12}$ branched alkyl, substituted or unsubstituted C$_{3-6}$ cycloalkyl, substituted or unsubstituted aryl, or aralkyl), thiol group (—SH), carboxyl group (—COOH), aldehyde group (—CHO), isocynato group (—N=C=O), sulfonic acid group (—SO$_3$H), sulfuric acid group (—OSO$_3$H), phosphoric acid group (—OPO$_3$H), phosphonic acid group (—PO$_3$H$_2$), allylic halide group, benzylic halide group, substituted benzylic halide group, and oxiranyl group (—CH(O)CH$_2$).

A therapeutic drug compound may be directly coupled to a lipophilic moiety (e.g., a tocopherol moiety) through an ester group (—C(=O)O—), carbamate group (—OC(=O)NH—), sulfonate group (—SO$_3$—), sulfate group (—OSO$_3$—), phosphate group (—OPO$_3$R$_1$—, where R$_1$ is independently selected from H, C$_{1-6}$ n-alkyl, C$_{3-12}$ branched alkyl, substituted or unsubstituted C$_{3-6}$ cycloalkyl, substituted or unsubstituted aryl, or aralkyl), phosphonate group (—PO$_3$R$_1$—, where R$_1$ is independently selected from H, C$_{1-6}$ n-alkyl, C$_{3-12}$ branched alkyl, substituted or unsubstituted C$_{3-6}$ cycloalkyl, substituted or unsubstituted aryl, or aralkyl), or ether group (—O—).

A tocopherol compound, a representative lipophilic compound suitable for making the compounds of the invention, includes a hydroxyl group (—OH). After modification, a tocopherol compound may be covalently coupled to a linker compound that includes one or more reactive functional groups. Suitable reactive functional groups include the following groups: hydroxyl group (—OH), amino group (primary amino group, —NH$_2$, or secondary amino group, —NHR$_1$, where R$_1$ is independently selected from H, C$_{1-6}$ n-alkyl, C$_{3-12}$ branched alkyl, substituted or unsubstituted C$_{3-6}$ cycloalkyl, substituted or unsubstituted aryl, or aralkyl.), thiol group (—SH), carboxyl group (—C(=O)OH), aldehyde group (—CHO), isocynato group (—N=C=O), sulfonic acid group (—SO$_3$H), sulfuric acid group (—OSO$_3$H), phosphoric acid group (—OPO$_3$H), phosphonic acid group (—PO$_3$H$_2$), allylic halide group, benzylic halide group, substituted benzylic halide group, and oxiranyl group (—CH(O)CH$_2$).

Linker Moieties. As noted above, in some embodiments, the compounds of the invention include a lipophilic moiety (e.g., tocopherol moiety) covalently coupled to a therapeutic drug moiety by a linker moiety. In addition to the embodiments described above, the tocopherol-modified therapeutic drug compounds of the invention can be represented by the general formula (8):

$$T\text{-}A\text{-}R\text{-}A'\text{-}D \qquad (8)$$

where T is a tocopherol moiety (i.e., a representative lipophilic moiety), D is a therapeutic drug moiety, and A-R-A' is a linker moiety. It will be appreciated that for formulae (1) and (3)–(7) above, each of which includes linker moiety L, the linker moiety L in those compounds can be linker moiety A-R-A'.

In formula 8, groups A and A' are independently selected from O, S, SO, SO$_2$, NR$_1$, carboxylate group (—C(=O)O—), amide group (—C(=O)NR$_1$—), anhydride group (—C(=O)OC(=O)—), carbamate group (—OC(=O)NH—), carbonyldioxy group (—OC(=O)O—), ureylene group (—NR$_1$C(=O)NR$_2$—), phosphate group (—OP(=O)(OR$_1$)O—), phosphamide group (—OP(=O)(NR$_1$)O—), phosphonate group (—OP(OR$_1$)O—), phosphonamide group (—OP(=O)NR$_1$—), sulfate group (—OSO$_2$O—), sulfamide group (—SO$_2$NR$_1$—), sulfonate group (—SO$_3$—), sulfonamide group (—SO$_2$NR$_1$—), and the dicarbonyl group, —C(=O)R$_3$C(=O)—, where R$_3$ is absent or a divalent alkyl (e.g., —(CH$_2$)$_n$—, n=1-12), substituted alkyl, branched alkyl, cycloalkyl, substituted cycloalkyl, aryl, substituted aryl. For the above groups, R is a divalent group selected from the following groups: alkyl; substituted alkyl, branched alkyl; cycloalkyl; substituted cycloalkyl; heteroalkyl; substituted heteroalkyl; aryl; substituted aryl; aralkyl; substituted aralkyl; amino acid; peptide; polypeptide; protein; mono-, di- or polysaccharide; oligomer of ethylene glycol, poly(ethylene glycol); poly(alkylene oxide) polymers, such as poly(ethylene oxide) and poly(propylene oxide); and poly(ethylene oxide)-poly(propylene oxide) copolymer. For the above groups, R$_1$ and R$_2$ are independently selected from Na$^+$, K$^+$, H, C$_{1-6}$ n-alkyl, C$_{3-12}$ branched alkyl, substituted or unsubstituted C$_{3-6}$ cycloalkyl, substituted or unsubstituted aryl, and substituted or unsubstituted aralkyl.

As used herein, the term "aryl" refers to monocyclic and polycyclic aromatic compounds having from 6 to 14 carbon or hetero atoms, and includes carbocyclic aryl groups and heterocyclic aryl groups. Representative aryl groups include phenyl, naphthyl, pyridinyl, pyrimidinyl, thiazolyl, indolyl, imidazolyl, furanyl, and the like. The term "aralkyl" refers to an alkyl group that is substituted with an aryl group.

The following compounds (compounds 9 to 32) are representative examples of compounds having formula 8.

A linker moiety (L) and therapeutic drug moiety (D) may be covalently coupled through an ester group. In one embodiment, the therapeutic drug moiety includes a hydroxyl group that is coupled with a carboxyl group of the linker moiety. The linker moiety may be coupled to a tocopherol moiety through an ether group (compound 9), ester group (compound 10), amine group (compound 11), or amide group (compound 12).

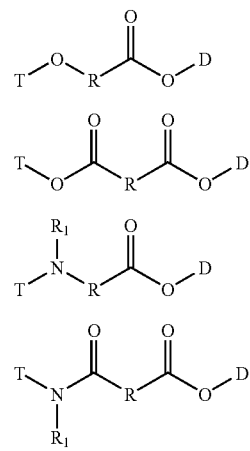

In another embodiment, the therapeutic drug moiety (D) includes a carboxyl group that is coupled with a hydroxyl group of the linker moiety (L). The linker moiety may be coupled to a tocopherol moiety through an ether group (compound 13), ester group (compound 14), amine group (compound 15), or amide group (compound 16).

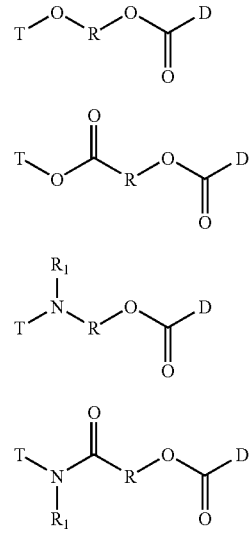

In the above compounds, divalent group R is selected from alkyl; substituted alkyl; branched alkyl; cycloalkyl; substituted cycloalkyl; heteroalkyl; substituted heteroalkyl; aryl; substituted aryl; aralkyl; substituted aralkyl; amino acid; peptide; polypeptide; protein; mono-, di- or polysaccharide; oligomer of ethylene glycol, poly(ethylene glycol); poly(alkylene oxide) polymers, such as poly(ethylene oxide) and poly(propylene oxide); and poly(ethylene oxide)-poly(propylene oxide) copolymer. In the above compounds, R$_1$ is selected from H, C$_{1-6}$ n-alkyl, C$_{3-12}$ branched alkyl, substituted or unsubstituted $C_{3-6}$ cycloalkyl, substituted or unsubstituted aryl, and substituted or unsubstituted aralkyl.

While the preferred embodiment of the invention has been illustrated and described, it will be appreciated that various changes can be made therein without departing from the spirit and scope of the invention. A linker moiety (L) and therapeutic drug moiety (D) may be covalently coupled through an amide group. In one embodiment, the therapeutic drug moiety includes an amine group that is coupled a carboxyl group of the linker moiety. The linker moiety may be coupled to a tocopherol moiety through an ether group (compound 17), ester group (compound 18), amine group (compound 19), or amide group (compound 20).

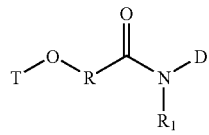

17

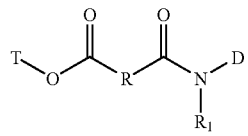

18

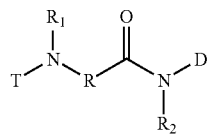

19

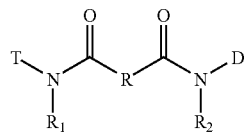

20

In the above compounds, divalent group R is selected from alkyl; substituted alkyl; branched alkyl; cycloalkyl; substituted cycloalkyl; heteroalkyl; substituted heteroalkyl; aryl; substituted aryl; aralkyl; substituted aralkyl; amino acid; peptide; polypeptide; protein; mono-, di- or polysaccharide; oligomer of ethylene glycol, poly(ethylene glycol); poly(alkylene oxide) polymers, such as poly(ethylene oxide) and poly(propylene oxide); and poly(ethylene oxide)-poly(propylene oxide) copolymer. In the above compounds, $R_1$ and $R_2$ are independently selected from H, $C_{1-6}$ n-alkyl, $C_{3-12}$ branched alkyl, substituted or unsubstituted $C_{3-6}$ cycloalkyl, substituted or unsubstituted aryl, and substituted or unsubstituted aralkyl.

A linker moiety (L) and a therapeutic drug moiety (D) may be covalently coupled through an ether group (compound 21) or amine group (compound 22). In one embodiment, the therapeutic drug moiety includes a hydroxy group, and in another embodiment, the therapeutic drug moiety includes an amine group. The linker moiety may be coupled to a tocopherol moiety through an ether group.

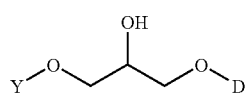

21

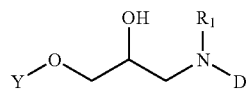

22

In the above compounds, $R_1$ is selected from H, $C_{1-6}$ n-alkyl, $C_{3-12}$ branched alkyl, substituted or unsubstituted $C_{3-6}$ cycloalkyl, substituted or unsubstituted aryl, or aralkyl.

A tocopherol moiety (T) and a therapeutic drug moiety (D) may be covalently coupled through a carbonyldioxy group (—OC(=O)O—) (compound 23). In this case, the linker moiety is the carbonyldioxy group and the therapeutic drug moiety includes a hydroxyl group.

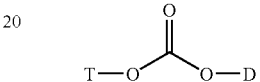

23

A tocopherol moiety (T) and a therapeutic drug moiety (D) may be covalently coupled through an anhydride group (—C(=O)OC(=O)—). In one embodiment, the therapeutic drug moiety includes a carboxyl group that is coupled with a carboxyl group of the linker moiety. The linker moiety may be coupled to a tocopherol moiety through an ether group (compound 24), ester group (compound 25), amine group (compound 26), or amide group (compound 27).

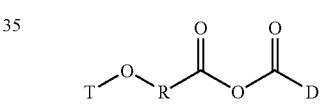

24

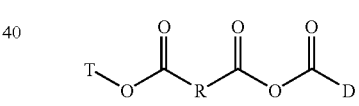

25

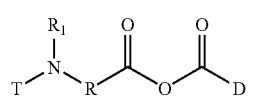

26

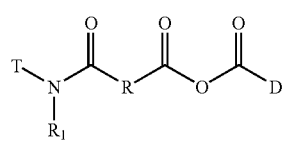

27

In the above compounds, divalent group R is selected from alkyl; substituted alkyl; branched alkyl; cycloalkyl; substituted cycloalkyl; heteroalkyl; substituted heteroalkyl; aryl; substituted aryl; aralkyl; substituted aralkyl; amino acid; peptide; polypeptide; protein; mono-, di- or polysaccharide; oligomer of ethylene glycol, poly(ethylene glycol); poly(alkylene oxide) polymers, such as poly(ethylene oxide) and polypropylene oxide); and poly(ethylene oxide)-polypropylene oxide) copolymer. In the above compounds, $R_1$ is selected from H, $C_{1-6}$ n-alkyl, $C_{3-12}$ branched alkyl, substituted or unsubstituted $C_{3-6}$ cycloalkyl, substituted or unsubstituted aryl, and substituted or unsubstituted aralkyl.

A tocopherol moiety (T) and therapeutic drug moiety (D) may be covalently coupled through a phosphate, phosphoramide, or thiophosphate group (compound 28).

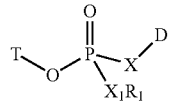

28

In the above compounds, X is O, $NR_2$, or S; $X_1$ is O, $NR_3$, or S; and $R_1$ is selected from $Na^+$, $K^+$, H, $C_{1-6}$ n-alkyl, $C_{3-12}$ branched alkyl, substituted or unsubstituted $C_{3-6}$ cycloalkyl, substituted or unsubstituted aryl, or aralkyl; and $R_2$ and $R_3$ are independently selected from $C_{1-6}$ n-alkyl, $C_{3-12}$ branched alkyl, substituted or unsubstituted $C_{3-6}$ cycloalkyl, substituted or unsubstituted aryl, or aralkyl.

A tocopherol moiety (T) and a therapeutic drug moiety (D) may be covalently coupled through a sulfate, thiosulfate, or sulfonamide group (compound 29).

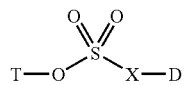

29

In the above compounds, X is O, $NR_1$, or S; and $R_1$ is selected from H, $C_{1-6}$ n-alkyl, $C_{3-12}$ branched alkyl, substituted or unsubstituted $C_{3-6}$ cycloalkyl, substituted or unsubstituted aryl, or aralkyl.

A tocopherol moiety (T) and therapeutic drug moiety (D) may be covalently coupled through a ureylene group (—NHC(=O)NH—) (compound 30).

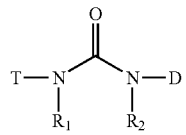

30

In the above compounds, $R_1$ and $R_2$ are independently selected from H, $C_{1-6}$ n-alkyl, $C_{3-12}$ branched alkyl, substituted or unsubstituted $C_{3-6}$ cycloalkyl, substituted or unsubstituted aryl, or aralkyl.

A tocopherol moiety (T) and a therapeutic drug moiety (D) may be covalently coupled through a carbamate group (—$NR_1$C(=O)O— or —OC(=O)$NR_2$—, compounds 31 and 32, respectively).

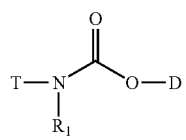

31

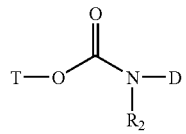

32

In the above compounds, $R_1$ and $R_2$ are independently selected from H, $C_{1-6}$ n-alkyl, $C_{3-12}$ branched alkyl, substituted or unsubstituted $C_{3-6}$ cycloalkyl, substituted or unsubstituted aryl, or aralkyl.

Lipophilic Moiety. The compounds of the invention include one or more lipophilic moieties. The lipophilic moiety or moieties increases the solubility of the compound in a lipophilic solvent or environment. In one embodiment, the lipophilic moiety is a tocopherol moiety.

As used herein, the term "tocopherol moiety" refers to a chemical moiety that is derived from a family of natural or synthetic compounds, also known by their generic names, tocol or vitamin E. In addition to tocopherol compounds, tocotrienol compounds are included in this family. These compounds include a chroman head having a phenolic alcohol (C-6) and a phytyl tail (C-2). These compounds have the following general formula:

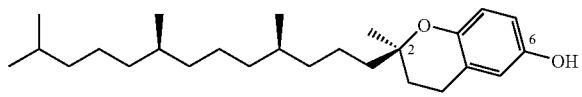

Tocopherols constitute a series of related benzopyranols (or methyl tocols) in which the C-2 phytyl (sixteen carbon) side chain is saturated. Representative tocopherols include α-tocopherol, (d-form, dl-form, l-form), β-tocopherol (d-form, dl-form, l-form), γ-tocopherol (d-form, dl-form, l-form), and δ-tocopherol (d-from, dl-form, l-form). Among tocopherols, α-tocopherol is the most abundant. Tocotrienols are similar in structure to tocopherols except that the trienols have three double bonds in the C-2 phytyl side chain.

Tocopherol and tocotrienol compounds useful in making the compounds of the invention include those shown below.

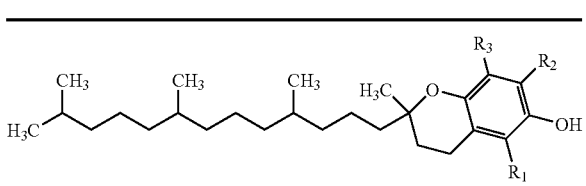

Tocopherol

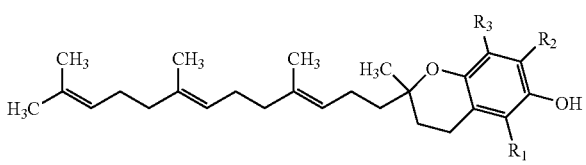

Tocotrienol

| Compound | $R_1$ | $R_2$ | $R_3$ |
|---|---|---|---|
| alpha (α) | $CH_3$ | $CH_3$ | $CH_3$ |
| beta (β) | $CH_3$ | H | $CH_3$ |
| gamma (γ) | H | $CH_3$ | $CH_3$ |
| delta (δ) | H | H | $CH_3$ |

As used herein, the term "tocopherol" refers to any member of the tocopherol family noted above.

Therapeutic Drug Moiety. The compounds of the invention include one or more therapeutic drug moieties. Virtually any therapeutic drug compound having a suitable functional group, or that can be modified to include a suitable functional group, can be covalently coupled to a lipophilic compound to provide a compound of the invention. Representative functional groups include, for example, hydroxyl groups (—OH), amino groups (primary amino groups, —NH$_2$, and secondary amino groups, —NHR), thiol groups (—SH), carboxyl groups (—COOH), aldehyde groups (—CHO), isocynato groups (—N=C=O), sulfonic acid groups (—SO$_3$H), sulfuric acid groups (—OSO$_3$H), phosphoric acid groups (—OPO$_3$H), phosphonate groups (—PO$_3$OR$_1$R$_2$, and R$_1$ and R$_2$ are independently selected from H, C$_{1-6}$ n-alkyl, C$_{3-12}$ branched alkyl, substituted or unsubstituted C$_{3-6}$ cycloalkyl, substituted or unsubstituted aryl, or aralkyl.), allylic halide group, benzylic halide group, substituted benzylic halide group, and oxiranyl group (—CH(O)CH$_2$).

Therapeutic drug compounds useful in making the compounds of the invention need not be substantially water insoluble, although tocopherol modification according to the present invention is especially well suited for formulating and delivering such water-insoluble compounds.

In one embodiment, the therapeutic drug moiety is derived from a therapeutic compound that is substantially insoluble in water. In another embodiment, the therapeutic drug moiety is derived from a therapeutic compound that is substantially insoluble in organic solvents. In another embodiment, the therapeutic drug moiety is derived from a therapeutic compound that is substantially insoluble in water and substantially insoluble in organic solvents. In one embodiment, the therapeutic drug compound has a solubility in water at room temperature less than about 1000 µg/mL. In one embodiment, the therapeutic drug compound has a solubility in water at room temperature less than about 500 µg/mL. In one embodiment, the therapeutic drug compound has a solubility in water at room temperature less than about 100 µg/mL. In one embodiment, the therapeutic drug compound has a solubility in water at room temperature less than about 25 µg/mL.

Representative therapeutic compound drugs useful in making the compounds of the invention include anticancer compounds (e.g., paclitaxel and its derivatives including docetaxel, camptothecin and its derivatives including 7-ethyl-10-hydroxycamptothecin (SN38) and 10-hydroxycamptothecin, and doxorubicin and its derivatives), antifungal compounds (e.g., flucanazole), antibacterial compounds (e.g., penicillin G, penicillin V), anti-hypertensive compounds (e.g., hydralazine, candesartan, and carvediol), anti-inflammatory compounds (e.g., isoxicam), antidiabetic compounds (e.g., metformin), antiviral compounds (e.g., lamivudine), antidepressant compounds (e.g., fluoxetine), antihistaminic compounds (e.g., hydroxyzine), anti-arrhythmic compounds (e.g., procainamide hydrochloride), anti-hyperlipoproteinemic compounds (e.g., probucol), and compounds for reproductive health (e.g., danazol), and treating Parkinson's disease (e.g., lazabemide), and immunosuppressive (e.g., azathioprine and cyclosporine) and respiratory (e.g., bosentan) diseases and conditions. Other therapeutically useful biological materials that can be modified according to the invention, include biologically active proteins, enzymes, and peptides.

In one embodiment, the therapeutic drug moiety is derived from an anticancer compound. Representative anticancer therapeutic compounds include taxanes. Taxanes include any anti-mitotic taxane, taxane derivative or analog. As used herein, the term "taxane" refers to taxanes, taxines, and taxoids, as well as derivatives or analogs thereof.

Paclitaxel and its derivatives and analogs are members of the taxane family. Paclitaxel derivatives include, for example benzoate derivatives of paclitaxel such as 2-debenzoyl-2-aroyl and C-2-acetoxy-C-4-benzoate paclitaxel, 7-deoxytaxol, C-4 aziridine paclitaxel, as well as various paclitaxel conjugates with natural and synthetic polymers, particularly with fatty acids, phospholipids, and glycerides and 1,2-diacyloxypropane-3-amine. Other paclitaxel derivatives include docetaxel; spicatin; taxane-2,13-dione, 5β,9β,10β-trihydroxy-, cyclic 9,10-acetal with acetone, acetate; taxane-2,13-dione, 5β,9β,10β-trihydroxy-, cyclic 9,10-acetal with acetone; taxane-2β,5β,9β,10β-tetrol, cyclic 9,10-acetal with acetone; taxane; cephalomannine-7-xyloside; 7-epi-10-deacetylcephalomannine; 10-deacetylcephalomannine; cephalomannine; taxol B; 13-(2',3'-dihydroxy-3'phenylpropionyl)baccatin III; yunnanxol; 7-(4-azidobenzoyl) baccatin III; N-debenzoyltaxol A; O-acetylbaccatin IV; 7-(triethylsilyl)baccatin III; 7,10-di-O-[(2,2,2,-trichloroethoxy)carbonyl]baccatin III; baccatin III 13-O-acetate; baccatin diacetate; baccatin; baccatin VII; baccatin VI; baccatin IV; 7-epi-baccatin III; baccatin V; baccatin I; baccatin III; baccatin A; 10-deactyl-7-epitaxol; epitaxol; 10-deacetyltaxol C; 7-xylosyl-10-deacetyltaxol; 10-deacetyltaxol-7-xyloside; 7-epi-10-deacetyltaxol; 10-deactyltaxol; or 10-deactyltaxol B.

Other anticancer compounds useful in making the compounds of the invention include camptothecin and its derivatives including 7-ethyl-10-hydroxycamptothecin (SN38) and 10-hydroxycamptothecin, and doxorubicin and its derivatives.

In certain embodiments, the therapeutic drug moiety is derived from paclitaxel, docetaxel, camptothecin, or their derivatives.

For compounds of the invention having formula (2) with m=1, formula (3) with n=1, and formula 8, certain compounds are excluded and are not within the scope of the invention. When the linker moiety is 2-hydroxypropylene (—CH$_2$CH(OH)CH$_2$—), the therapeutic drug moiety is not an α-amino acid (e.g., glycine, alanine, proline, cysteine, aminobutyric acid, aspartic acid, glutamic acid), an ω-amino acid (e.g., β-alanine, γ-aminobutyric acid, ε-aminocaproic acid, 2-aminoethanesulfonic acid (taurine)), or a peptide containing a cysteine residue bonding through its N-terminus or thiol group (e.g.,-glutathione). When the linker moiety is a succinate, the therapeutic drug moiety is not an S-linked amino or amino acid compound coupled to one of the aliphatic succinate carbons. When the linker moiety is succinate, the therapeutic drug moiety is not ferulic acid or an ester thereof.

In another aspect, methods for making the compounds of the invention are provided. There are many ways to covalently couple a lipophilic compound (e.g., a tocopherol compound) to a therapeutic drug compound to form a compound of the invention. In one embodiment, a representative tocopherol, d-α-tocopherol, includes a hydroxyl group that may be directly coupled with a carboxyl group of a therapeutic drug to form a tocopherol-modified therapeutic drug compound. The preparation of a representative tocopherol-modified therapeutic compound of the invention from a carboxylic acid-containing therapeutic drug compound is illustrated in FIG. 1.

In another embodiment, a tocopherol may be functionalized at the hydroxyl group with a reagent to attach an active group such as phosphoric chloride (—P(O)OR$_1$Cl), phosphonic chloride (—P(O)R$_1$Cl), sulfonic chloride (—SO$_2$Cl), or carbonyl chloride (—COCl). The resulting acid chloride can then be reacted with an appropriately functionalized therapeutic drug compound to provide a tocopherol-modified therapeutic drug compound.

Figure 2:
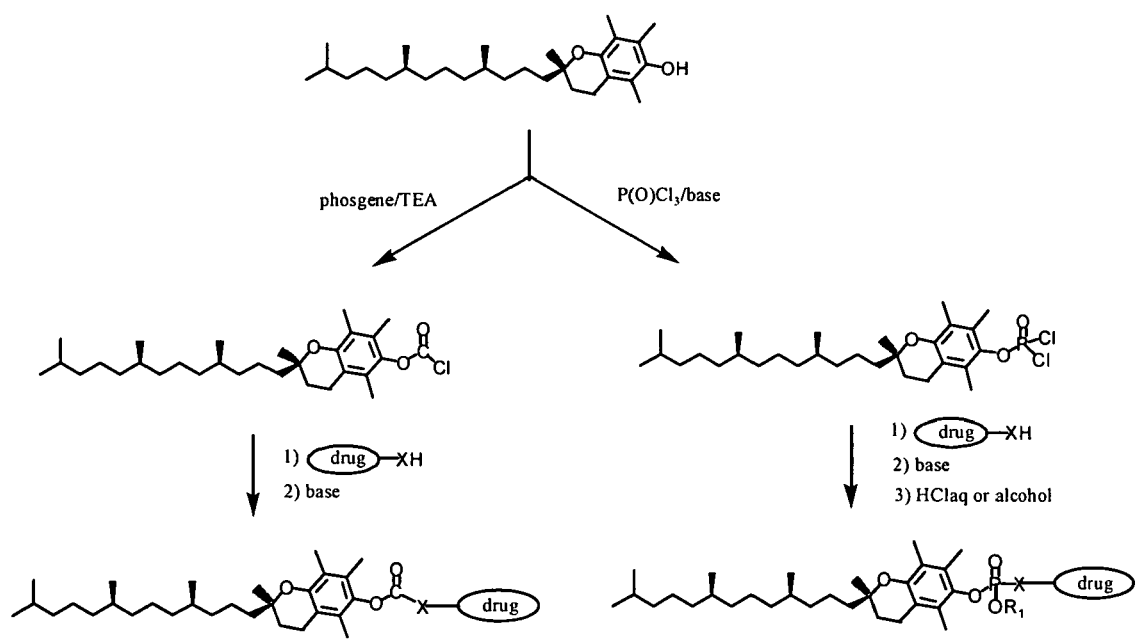
FIG. 2 schematically illustrates tocopherol functionalization with a carbonyl chloride group (—C(=O)Cl) and a phosphoric chloride group (—P(=O)OR$_1$Cl), and reaction of the resulting acid chloride and an appropriately functionalized therapeutic drug compound to provide a tocopherol-modified therapeutic drug compound.

In FIG. 2, X is O, S, or NH; and $R_1$ is independently selected from H, $C_{1-6}$ n-alkyl, $C_{3-12}$ branched alkyl, substituted or unsubstituted $C_{3-6}$ cycloalkyl, substituted or unsubstituted aryl, and substituted or unsubstituted aralkyl.

Figure 3:
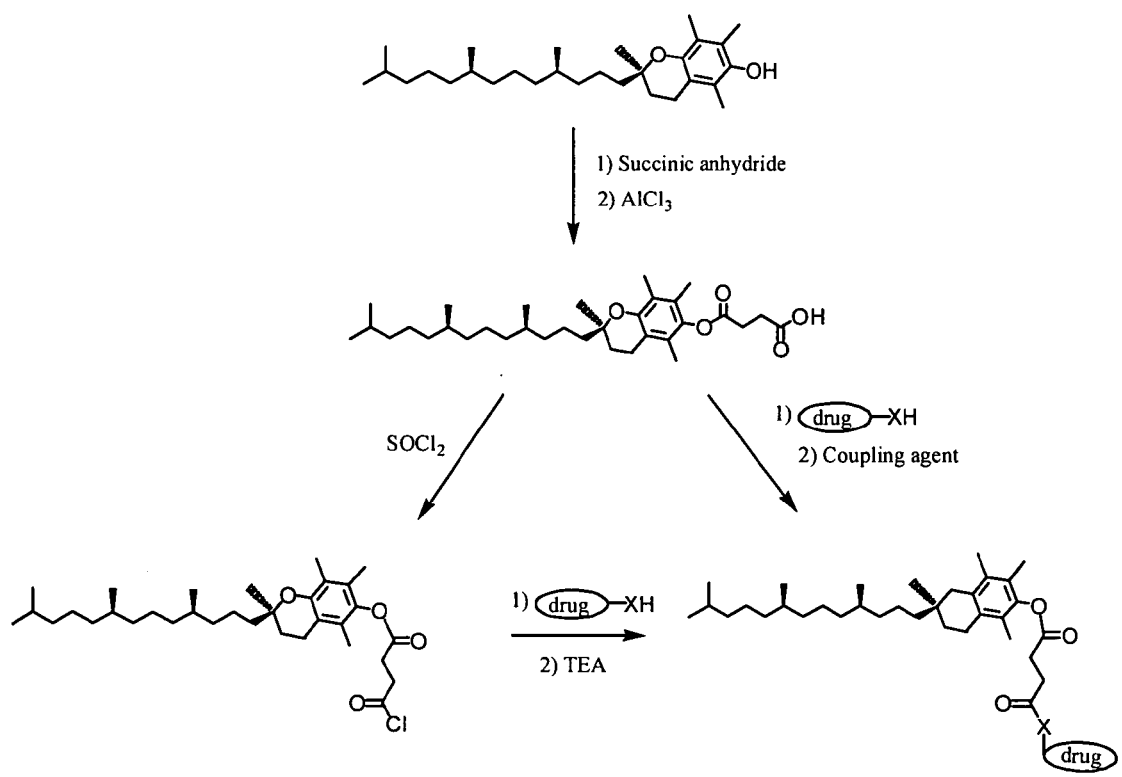
FIG. 3 schematically illustrates tocopherol functionalization with a dicarboxylic anhydride (succinic anhydride), and reaction of the resulting carboxylic acid and an appropriately functionalized therapeutic drug compound to provide a tocopherol-modified therapeutic drug compound.

In another embodiment, a tocopherol may be functionalized at the hydroxyl group with a dicarboxylic acid, ester, or anhydride reagent. Suitable reagents include succinic acid anhydride, 1,2-cyclohexanedicarboxylic anhydride, 2,3-dimethylsuccinic anhydride, 3,3-tetramethylene glutaric anhydride, glutaric anhydride, maleic acid anhydride, phthalic acid anhydride, terephthalic acid, or isophthalic acid to attach a carboxy group (—COOH). The resulting carboxyl group may then be directly reacted with an appropriately functionalized therapeutic drug or the carboxyl group may be converted to a more reactive carbonyl chloride group (—COCl), and then the carbonyl chloride group may be coupled with the functional group of the therapeutic drug to form a tocopherol-modified therapeutic drug compound as illustrated in FIG. 3. In FIG. 3, X is O, S, NH, or C(=O)O.

In another embodiment, a linker can be coupled to the hydroxyl group of a tocopherol and then a therapeutic drug can be coupled to an accessible functional group on the linker. The functional group may be, for example, but not limited to, a carboxyl group (—COOH), a poly(ethylene oxide) group (—(CH$_2$CH$_2$O)$_n$—H), an aldehyde group (—CHO), an isocyanato group (—N=C=O), a phosphoric acid group (—OPO$_3$H$_2$), or phosphoric chloride group (—OPO$_2$R$_1$Cl, where $R_1$ is a substituted or unsubstituted alkyl or cycloalkyl, a substituted or unsubstituted aryl, or an aralkyl), a phosphonic chloride group (—PO$_2$R$_1$Cl, where $R_1$ is a substituted or unsubstituted alkyl or cycloalkyl, a substituted or unsubstituted aryl, or an aralkyl), a sulfuric acid group (—OSO$_3$H$_2$), a chlorosulfuric group (—SO$_3$Cl), or an oxiranyl group (—CH(O)CH$_2$).

The syntheses of representative tocopherol-modified therapeutic drug compounds of the invention are illustrated in FIGS. 4–11 and described in Examples 1–13.

Figure 4:
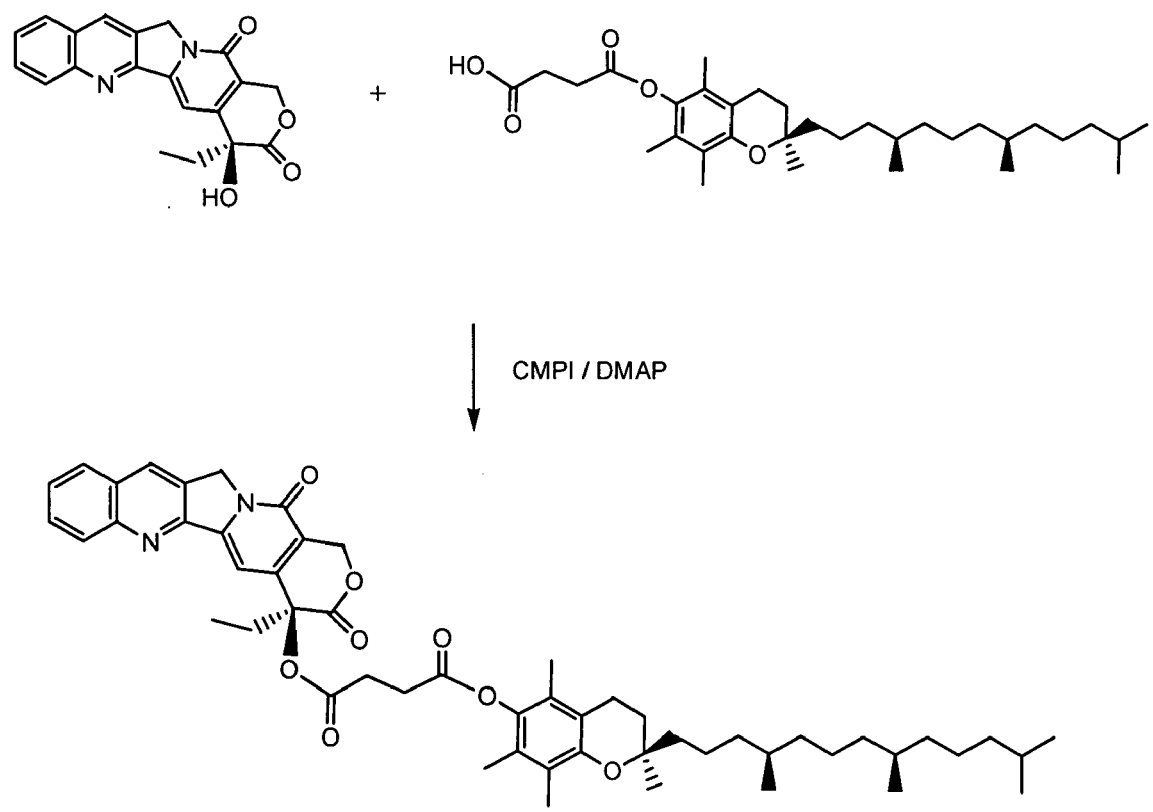
FIG. 4 schematically illustrates the preparation of tocopherol succinate camptothecin.

FIG. 4 illustrates the preparation of a tocopherol succinate cainptothecin compound. Tocopherol succinic acid (vitamin E succinic acid) has a free carboxy group that can couple with a hydroxyl group, amino group, thiol group, or carbonyl chloride group to provide a tocopherol-modified therapeutic drug having a succinate group as a linker. In FIG. 4, the carboxyl group of tocopherol acid succinate is coupled with the hydroxyl group of camptothecin. The preparation of tocopherol succinate camptothecin (Butanedioic acid, (2R)-3,4-dihydro-2,5,7,8-tetramethyl-2-[(4R, 8R)-4,8,12-trimethyltridecyl]-2H-1-benzopyran-6-yl (4S)-4-ethyl-3,4,12,14-tetrahydro-3,14-dioxo-1H-pyrano[3',4':6,7]indolizino[1,2-quinolin-4-yl ester) is described in Example 1.

Figure 5:
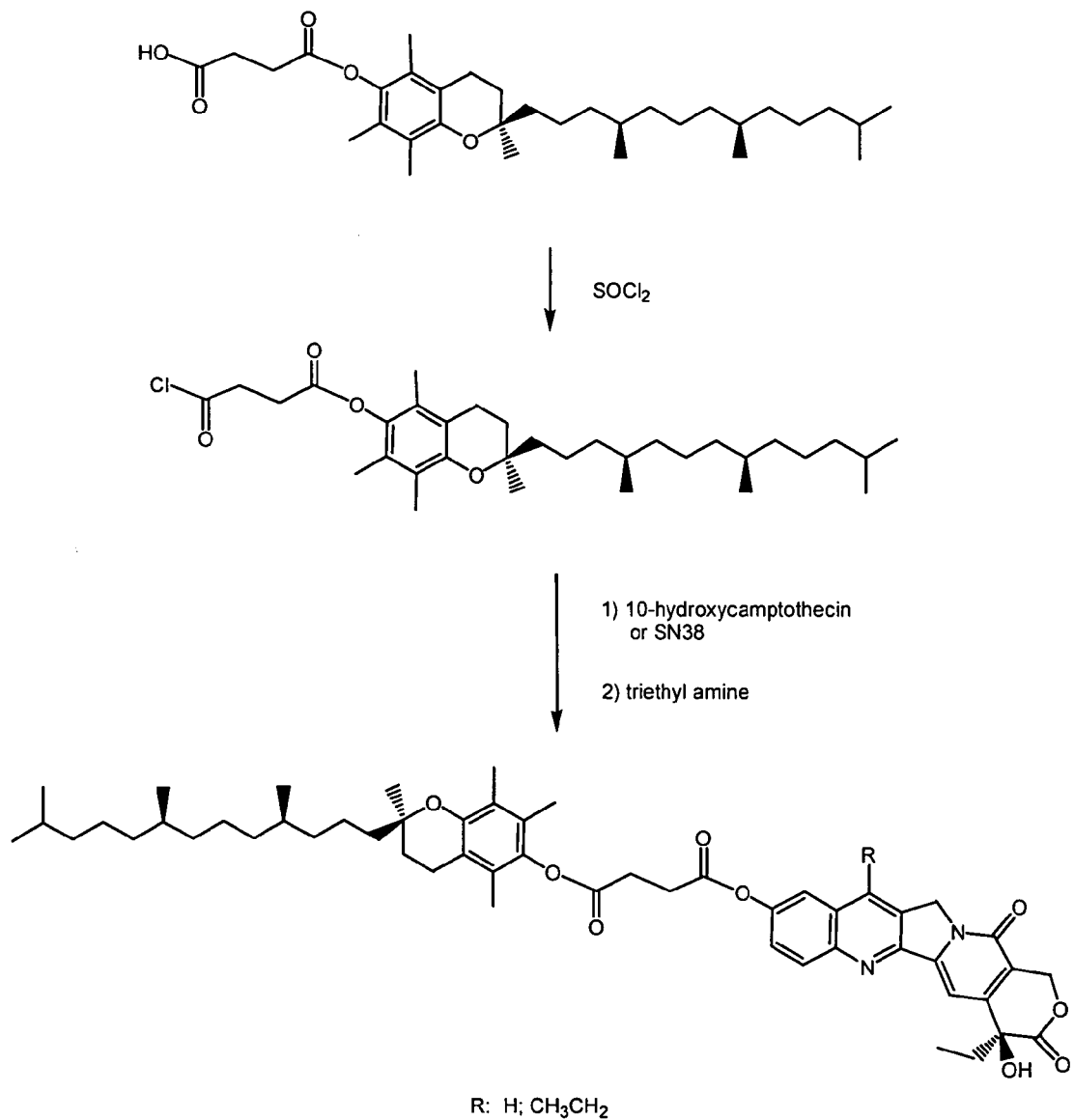
FIG. 5 schematically illustrates the preparations of tocopherol succinate 10-hydroxycamptothecin and tocopherol succinate 7-ethyl-10-hydroxycamptothecin.

FIG. 5 illustrates the preparation of tocopherol succinate 10-hydroxycamptothecin and tocopherol succinate 7-ethyl-10-hydroxycamptothecin (SN38). Tocopherol succinic acid is converted to the corresponding acid chloride, and then reacted with 10-hydroxycampiothecin or 7-ethyl-10-hydroxycamptothecin (SN38). The preparations of tocopherol succinate 10-hydroxycamptothecin (Butanedioic acid, (2R)-3,4-dihydro-2,5,7,8-tetramethyl-2-[(4R,8R)-4,8,12-trimethyltridecyl]-2H-1-benzopyran-6-yl (4S)-4-ethyl-3,4,12,14-tetrahydro-4-hydroxy-3,14-dioxo-1H-pyranol[3',4':6,7]indolizino[1,2-b]quinolin-9-yl ester) and tocopherol succinate 7-ethyl-10-hydroxycamptothecin (Butanedioic acid, (4S)-4,11-diethyl-3,4,12,14-tetrahydro-4-hydroxy-3,14-dioxo- 1H-pyrano[3',4':6,7]indolizino1,2-b]quinolin-9-yl (2R)-3,4-dihydro-2,5,7,8-tetramethyl-2-[(4R,8R)-4,8,12-trimethyltridecyl]-2H-1-benzopyran-6-yl ester) are described in Examples 2 and 3, respectively.

Figure 6:
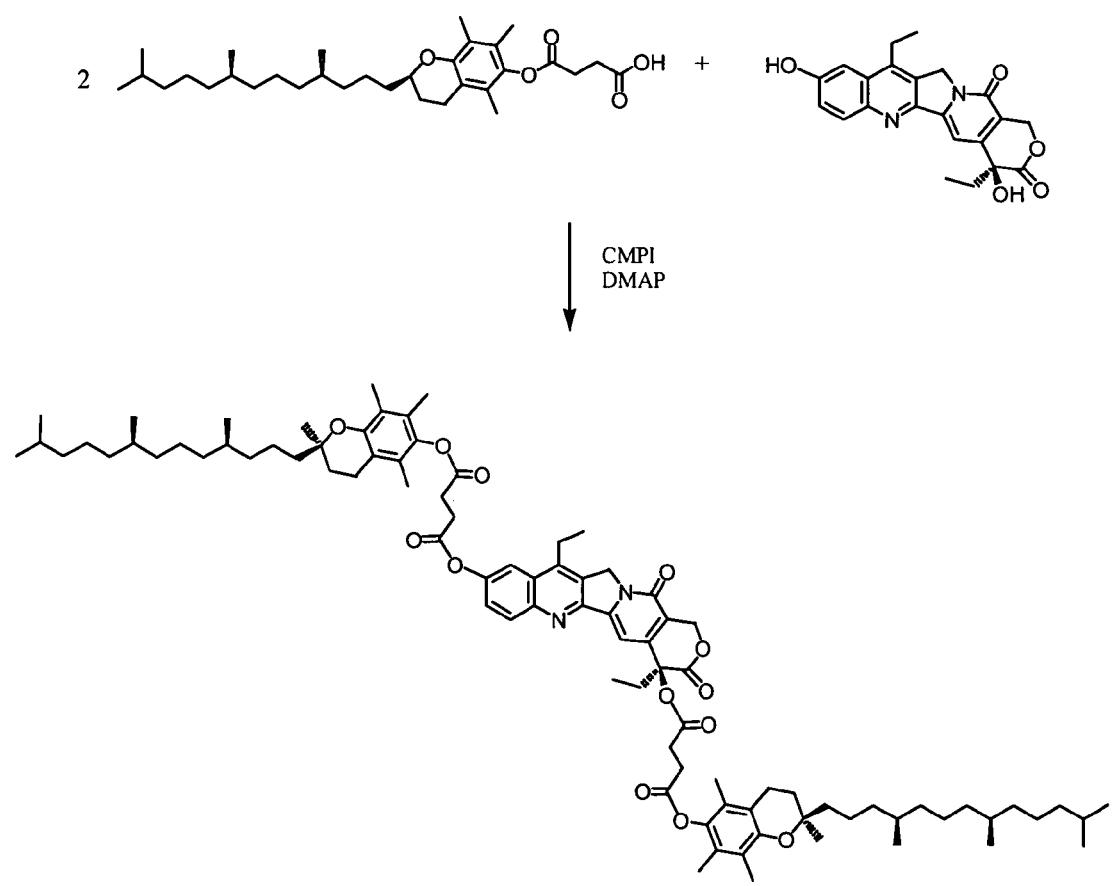
FIG. 6 schematically illustrates the preparation of 10,20-di(tocopherol succinate) 7-ethyl-10-hydroxycamptothecin.

FIG. 6 illustrates the preparation of 10,20-di(tocopherol succinate) SN38, which contains one therapeutic drug (SN38) moiety, two tocopherol moieties, and two linker moieties (succinyl groups). The preparation of 10,20-di(tocopherol succinate) SN38 is described in Example 4.

Figure 7:
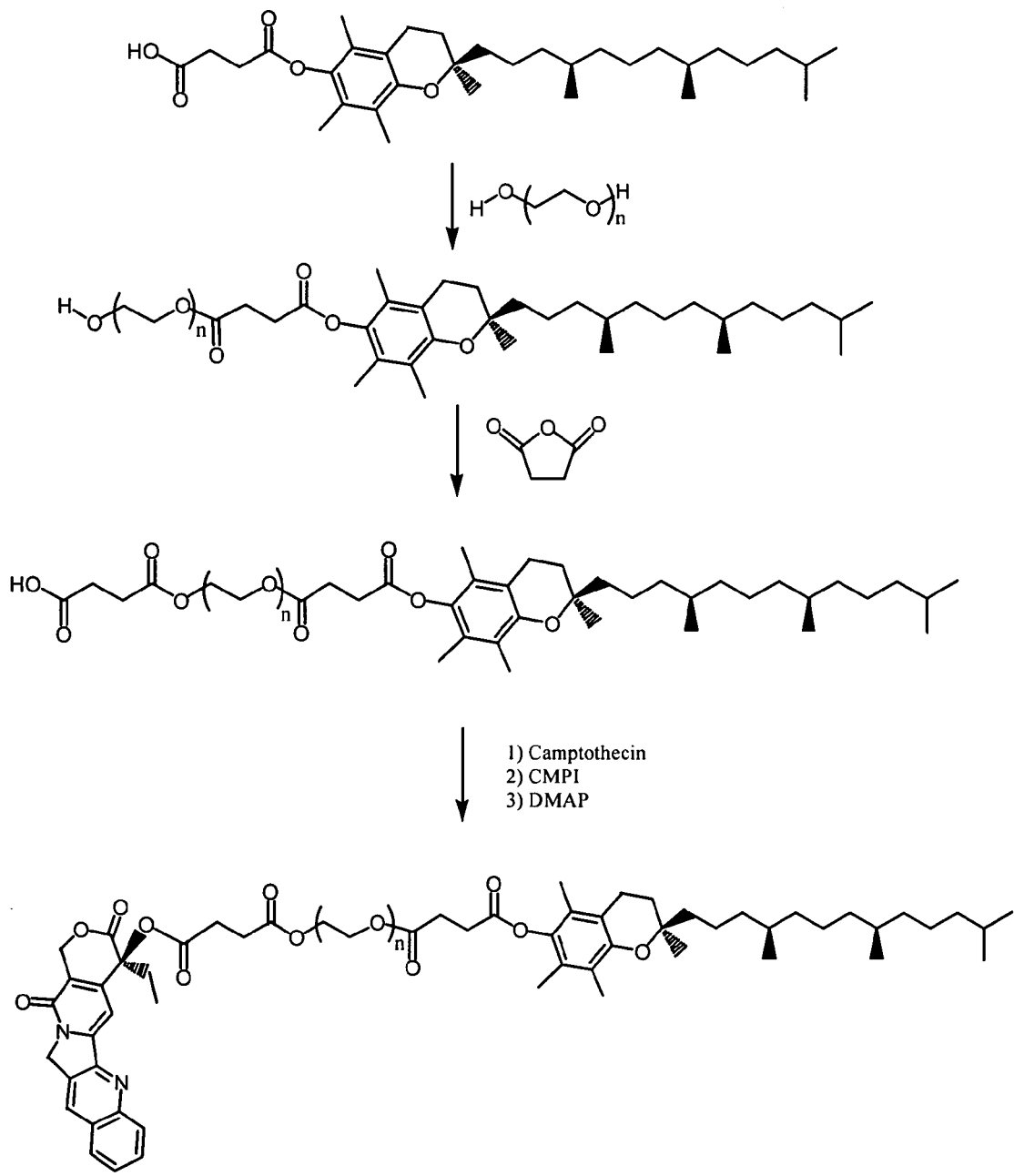
FIG. 7 schematically illustrates the preparation of tocopherol succinate camptothecin containing a poly(ethylene oxide) group.

Suitable linker moieties can include an oligomer or polymer such as a peptide, polypeptide, protein, mono-, di- or polysaccharide, oligomer of ethylene glycol, poly(ethylene glycol), poly(alkylene oxide) such as poly(ethylene oxide) and poly(propylene oxide), or poly(ethylene oxide)-poly (propylene oxide) copolymer. FIG. 7 illustrates the preparation of a tocopherol-modified camptothecin containing a linker moiety that includes a poly(ethylene oxide) group. The preparation of the tocopherol succinate camptothecin having a linker moiety that includes a poly(ethylene oxide) group is described in Example 5.

Figure 8:
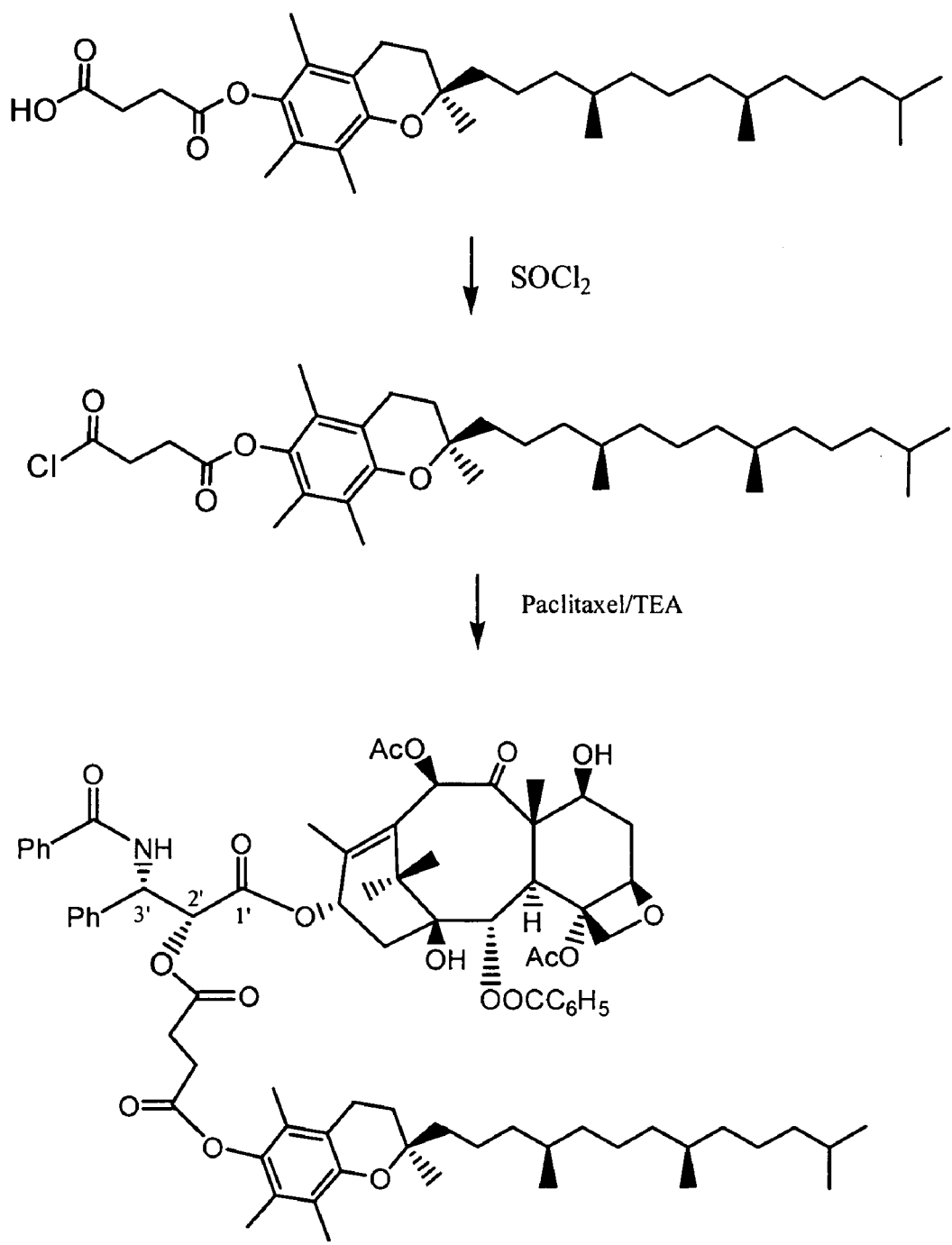
FIG. 8 schematically illustrates the preparation of tocopherol succinate paclitaxel.
Figure 9:
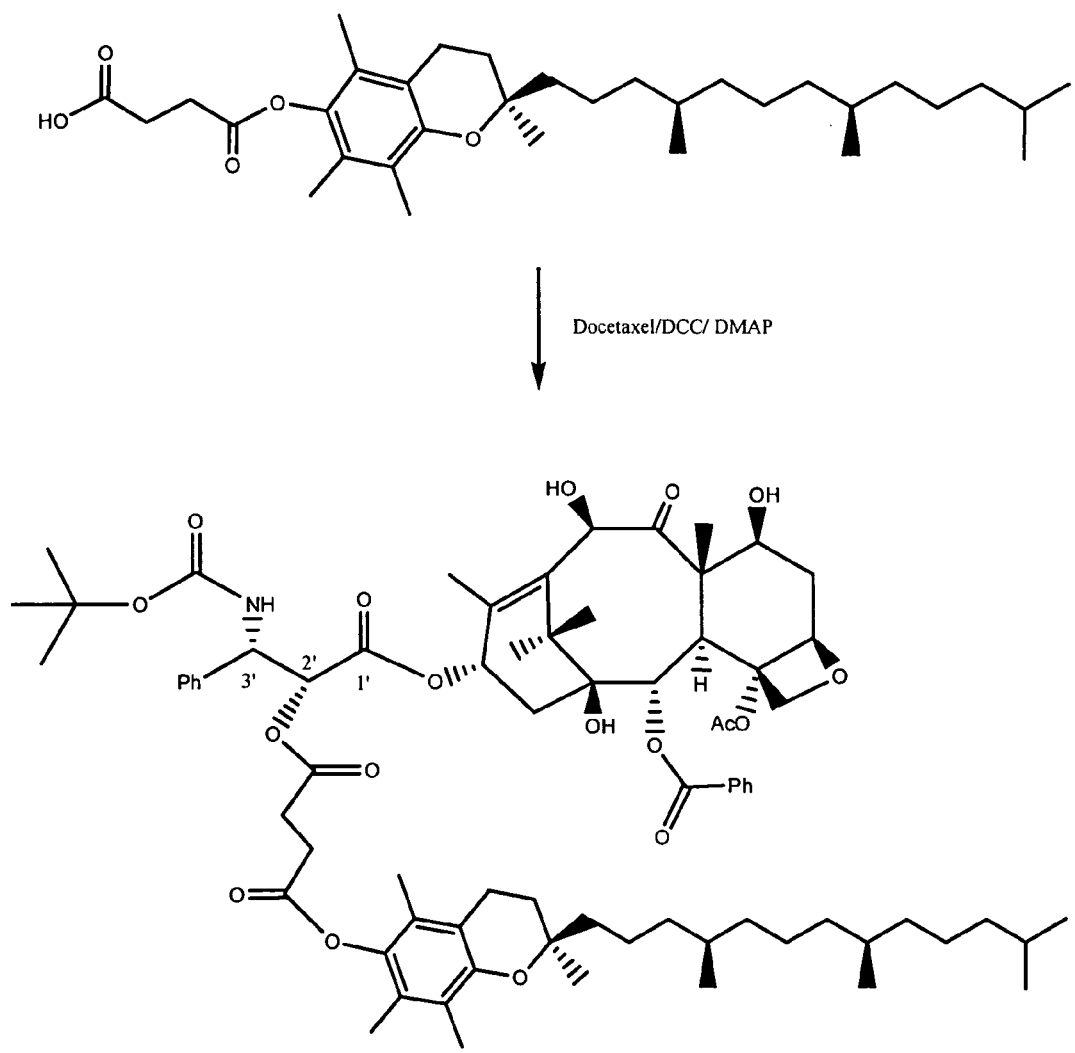
FIG. 9 schematically illustrates the preparation of tocopherol succinate docetaxel.

FIG. 8 illustrates the preparation of tocopherol succinate paclitaxel. In the preparation, tocopherol succinic acid is converted to the corresponding acid chloride and then reacted with paclitaxel. The preparation of tocopherol succinate paclitaxel is described in Example 6. FIG. 9 illustrates the preparation of tocopherol succinate docetaxel. The preparation of tocopherol succinate docetaxel is described in Example 7.

Figure 10:
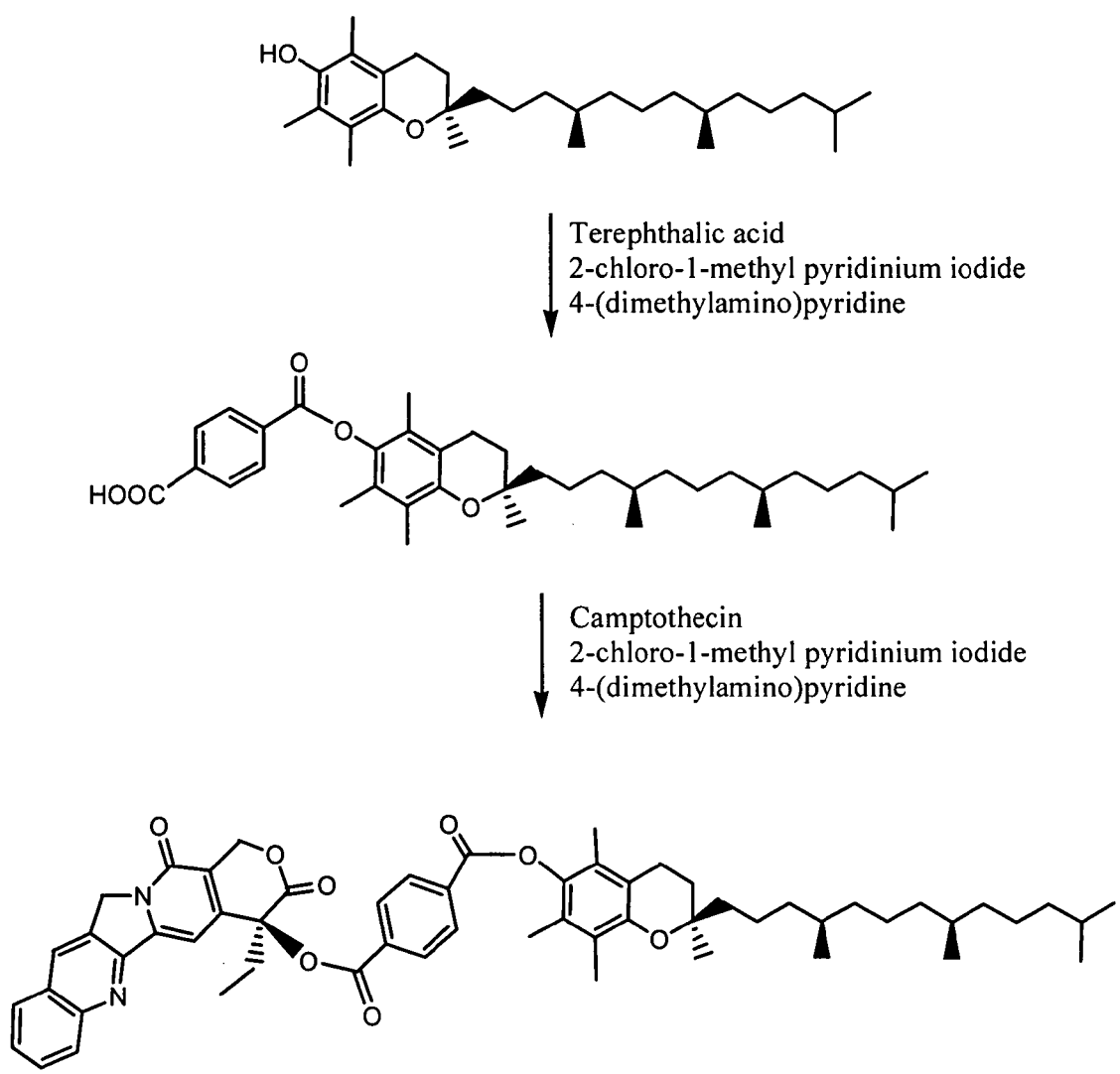
FIG. 10 schematically illustrates the preparation of tocopherol terephthlate camptothecin.

FIG. 10 illustrates the preparation of tocopherol terephthalate camptothecin. In the preparation, tocopherol is first conjugated with terephthalate to form tocopherol terephthalate (Example 9) and is then coupled with camptothecin to form tocopherol terephthalate camptothecin. The preparation of tocopherol terephthalate camptothecin is described in Example 10.

Figure 11:
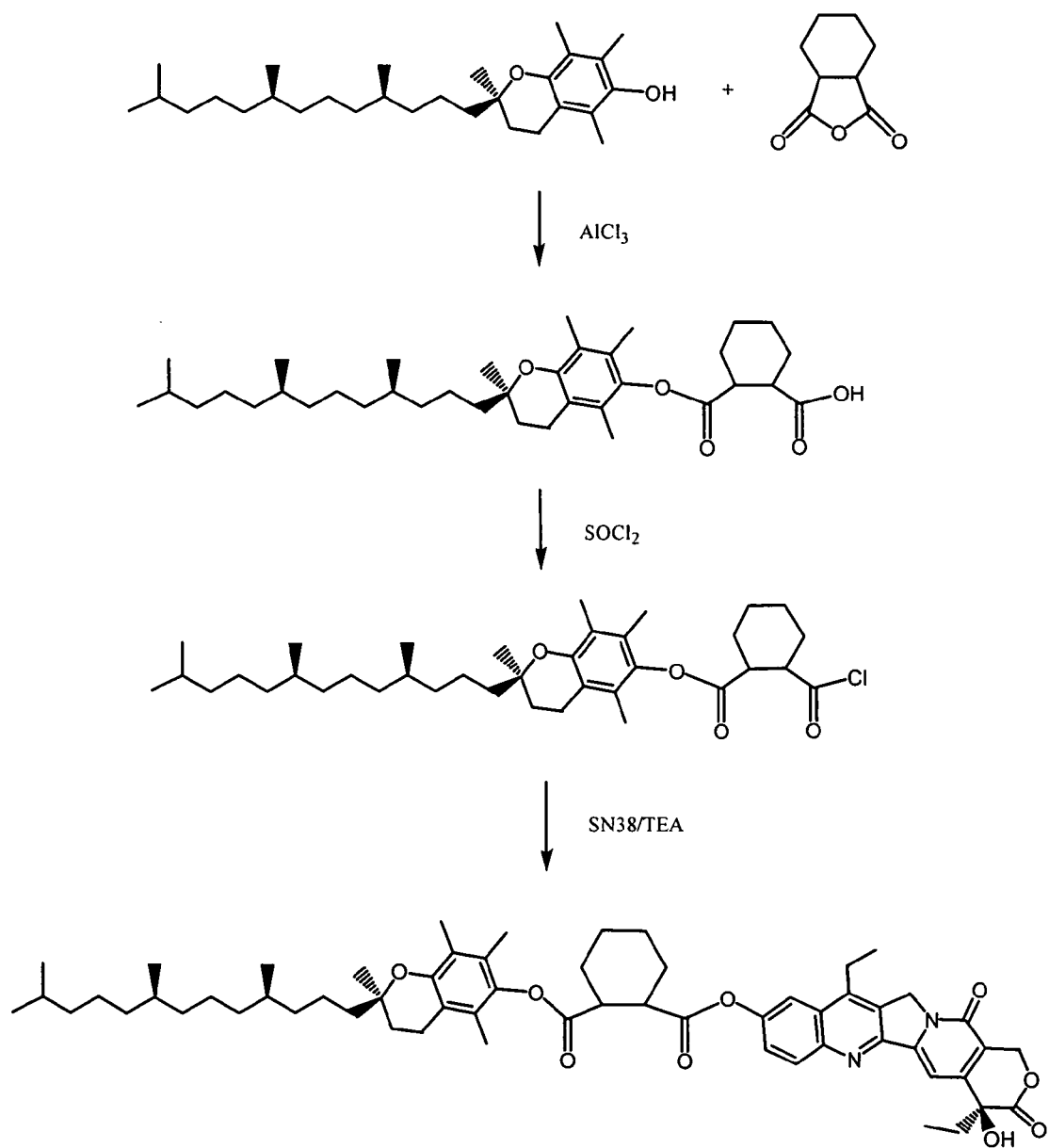
FIG. 11 schematically illustrates the preparation of tocopherol cyclohexane-1,2-dicarboxylate 7-ethyl-10-hydroxycamptothecin.

FIG. 11 illustrates the preparation of tocopherol cyclohexane-1,2-dicarboxylate SN38. The preparation of tocopherol cyclohexane-1,2-dicarboxylate SN38 is described in Example 11.

The preparations of tocopherol succinate doxorubicin and tocopherol succinate hydroxyzine are described in Examples 12 and 13, respectively.

In another aspect, the present invention provides compositions that include the compounds of the invention. The compositions include one or more compounds of the invention, optionally one or more additional therapeutic agents, and a lipophilic medium. In one embodiment, a tocopherol-modified therapeutic drug compound is dissolved in the lipophilic medium. Because of the lipophilic moiety, the compound has improved lipophilicity compared to the unmodified therapeutic drug compound. The lipophilic medium (or carrier) of the composition can be any one of a variety of lipophilic mediums including, for example, oils. In one embodiment, the lipophilic medium includes a tocopherol (e.g., α-tocopherol). Representative oils useful as the lipophilic medium include the following:

Fatty acids and esters thereof, including carboxylic acids of various chain lengths, mostly straight chain, but which could be branched, examples of which include capric, caprylic, caproic, lauric, myristic, stearic, oleic, linoleic, behenic, and as well as saturated or unsaturated fatty acids and esters;

Fatty acids esterified with glycerin to form mono-, di-, or triglycerides, which can be synthetic or derived from natural sources, including, but not limited to, for example, glycerides such as soybean oil, cottonseed oil, rapeseed oil, fish oil, castor oil, Capmul MCM, Captex 300, Miglyol 812, glyceryl monooleate, triacetin, acetylated monoglyceride, tristearin, glyceryl behenate, and diacetyl tartaric acid esters of monoglycerides;

Glycerides conjugated to other moieties, such as polyethylene glycol (for example, Labrasol, Labrafac, Cremophor EL);

Phospholipids, either natural or synthetic, such as dimyristyl phosphatidylcholine, egg lecithin, and pegylated phospholipids;

Other fatty esters including fatty alcohols (myristyl myristate, isopropyl palmitate), or sugars (sorbitan monooleate, SPAN 80, Tween 80, sucrose laurate);

Fatty alcohols such as stearyl alcohol, lauryl alcohol, benzyl alcohol, or esters or ethers thereof, such as benzyl benzoate;

Fat-soluble vitamins and derivatives, for example, vitamin E (including all of the tocopherols and tocotrienols, and tocopherol and tocotrienol derivatives, such as vitamin E succinate, vitamin E acetate, and vitamin E succinate polyethylene glycol (TPGS)).

Organic co-solvents can also be used in the compositions, optionally in combination with water, including for example, ethanol, polyethylene glycol, propylene glycol, glycerol, N-methylpyrrolidone, and dimethyl sulfoxide.

The solubilities of two representative tocopherol-modified camptothecin compounds of the invention in several mediums are compared to camptothecin in Example 14.

In a further aspect, the invention provides emulsion, microemulsion, and micelle formulations that include a compound of the invention. Methods for making the emulsion, microemulsion, and micelle formulations are also provided.

As used herein, the term "emulsion" refers to a colloidal dispersion of two immiscible liquids, such as an oil and water, in the form of droplets, whose diameter, in general, are between 0.1 and 3.0 microns and which is typically optically opaque, unless the dispersed and continuous phases are refractive index matched. Such systems possess a finite stability, generally defined by the application or relevant reference system, which may be enhanced by the addition of amphiphilic molecules or viscosity enhancers.

The term "microemulsion" refers to a thermodynamically stable isotropically clear dispersion of two immiscible liquids, such as an oil and water, stabilized by an interfacial film of surfactant molecules. The microemulsion has a mean droplet diameter of less than 200 nm, in general between 10–50 nm. In the absence of water, mixtures of oil(s) and non-ionic surfactant(s) form clear and isotropic solutions that are known as self-emulsifying drug delivery systems (SEDDS) and can be used to improve lipophilic drug dissolution and oral absorption.

The emulsion and microemulsion formulations include an oil phase and an aqueous phase. The emulsion or microemulsion can be an oil-in-water emulsion or a water-in-oil emulsion. The oil phase includes one or more compounds of the invention and a lipophilic medium, as described above. In one embodiment, the compound is present in the formulation in an amount from about 0.005 to about 3.0 weight percent based on the total weight of the formulation. In one embodiment, the compound is present in the formulation in an amount from about 0.01 to about 2.5 weight percent based on the total weight of the formulation. In one embodiment, the compound is present in the formulation in an amount from about 0.1 to about 1.5 weight percent based on the total weight of the formulation. In one embodiment, the lipophilic medium is present in the formulation in an amount from about 2 to about 20 weight percent based on the total weight of the formulation. In one embodiment, the lipophilic medium is present in the formulation in an amount from about 4 to about 12 weight percent based on the total weight of the formulation. In one embodiment, the lipophilic medium is present in the formulation in an amount from about 6 to about 10 weight percent based on the total weight of the formulation.

In one embodiment of the emulsion or microemulsion, the compound is a tocopherol-modified therapeutic drug compound, the lipophilic medium includes a tocopherol, and the aqueous medium is water.

In addition to the compounds of the invention, the emulsion or microemulsion formulations can include other components commonly used in emulsions an microemulsions, and particularly used in pharmaceutical emulsions and microemulsions. These components include surfactants and co-solvents, among others. Representative surfactants include nonionic surfactants such as surface active tocopherol derivatives and surface active polymers.

Suitable surface active tocopherol derivatives include tocopherol polyethylene glycol derivatives, such as vitamin E succinate polyethylene glycol (e.g., d-α-tocopherol polyethylene glycol 1000 succinate, TPGS), which is a vitamin E derivative in which a polyethylene glycol is attached by a succinic acid ester at the ring hydroxyl of vitamin E. As used herein, "vitamin E succinate polyethylene glycol" includes vitamin E succinate polyethylene glycol and derivatives of vitamin E polyethylene glycol having various ester and ether links. TPGS is a non-ionic surfactant (HLB=16–18). TPGS is reported to inhibit P-glycoprotein, a protein that contributes to the development of multi-drug resistance. Embodiments of the formulations of the invention that include TPGS therefore include a P-glycoprotein inhibitor. Surface active tocopherol derivatives (e.g., TPGS) can be present in the formulations of the invention in an amount from about 1 to about 10 weight percent, about 2 to about 6 weight percent, or about 5 weight percent, based on the total weight of the formulation.

Suitable nonionic surfactants include block copolymers of ethylene oxide and propylene oxide known as POLOXAMERS or PLUROINICS. These synthetic block copolymers of having the general structure: $H(OCH_2CH_2)_a(OC_3H_6CH_2)_b(OCH_2CH_2)_aOH$. The following variants based on the values of a and b are commercially available from BASF Performance Chemicals (Parsippany, N.J.) under the trade name PLURONIC and consist of the group of surfactants designated by the CTFA name of POLOXAMER 108, 188, 217, 237, 238, 288, 338, 407, 101, 105, 122, 123, 124, 181, 182, 183, 184, 212, 231, 282, 331, 401, 402, 185, 215, 234, 235, 284, 333, 334, 335, and 403. For the most commonly used POLOXAMERS 124, 188, 237, 338, and 407 the values of a and b are 12/20, 79/28, 64/37, 141/44 and 101/56, respectively. In one embodiment the nonionic surfactant is present in the formulation in an amount from about 0.5 to about 5 weight percent based on the total weight of the formulation.

Co-solvents useful in the formulations include ethanol, polyethylene glycol, propylene glycol, glycerol, N-methylpyrrolidone, dimethylamide, and dimethylsulfoxide, among others. Polyethylene glycol (PEG) is a hydrophilic, polymerized form of ethylene glycol, consisting of repeating units having the chemical structure: ($-CH_2CH_2O-$). The general formula for polyethylene glycol is $H(OCH_2CH_2)_nOH$. The molecular weight ranges from 200 to 10,000. Such various forms are described by their molecular weights, for example, PEG-200, PEG-300, PEG-400, and the like.

Paclitaxel emulsions and their components are described in U.S. Pat. No. 6,458,173 and U.S. Pat. No. 6,660,286, each expressly incorporated herein by reference in its entirety.

Representative emulsions including tocopherol-modified therapeutic drug compounds (e.g., tocopherol succinate docetaxel, tocopherol succinate paclitaxel, tocopherol succinate camptothecin, tocopherol succinate 7-ethyl-10-hydroxycamptothecin, and tocopherol succinate 10-hydroxycamptothecin) are described in Example 15. In vitro cytotoxicities of representative tocopherol-modified therapeutic drug compounds (e.g., tocopherol succinate 7-ethyl-10-hydroxycamptothecin and tocopherol succinate camptothecin) are described in Example 16.

In a further aspect, the invention provides micelle formulations that include a compound of the invention and an aqueous phase. Micelles are organized aggregates of one or more surfactants in solution. In one embodiment, the compound is present in the formulation in an amount from about 0.005 to about 3.0 weight percent based on the total weight of the formulation. In one embodiment, the compound is present in the formulation in an amount from about 0.01 to about 2.5 weight percent based on the total weight of the formulation. In one embodiment, the compound is present in the formulation in an amount from about 0.1 to about 1.0 weight percent based on the total weight of the formulation. Suitable surfactants include those noted above, and in the amounts noted above. In one embodiment of the micelle formulation, the compound is a tocopherol-modified therapeutic drug compound and the surfactant is tocopherol polyethylene glycol succinate (TPGS). Representative micelle formulations including tocopherol-modified therapeutic drug compounds are described in Example 15.

The micelle formulation can also include additional components such as co-solvents including those noted above. In one embodiment, the micelle formulation includes a polyethylene glycol and a lower alkyl alcohol (e.g., ethanol). In one embodiment, the co-solvents are present in an amount from about 2 to about 20 weight percent based on the total weight of the formulation. The micelle, emulsion, and microemulsion formulations include an aqueous phase. In one embodiment, the aqueous phase includes deionized water. In another embodiment, the aqueous phase includes saline. In another embodiment, the aqueous phase is saline buffered with an organic acid (e.g., succinate, citrate).

The invention also provides the use of the compounds of the invention in the manufacture of a medicament. For example, for compounds of the invention that include a therapeutic drug moiety derived from a therapeutic drug compound effective in treating cell proliferative disease, the invention provides the use of such compounds in the manufacture of a medicament for the treatment of cell proliferative disease.

In other aspects, methods for administering a compound of the invention to a subject in need thereof, and methods for treating a condition treatable by administration of a therapeutically effective amount of a compound of the invention are also provided. These methods include the administration of the compounds, compositions, emulsion formulations, microemulsion formulations, and micelle formulations described herein.

In one embodiment, the invention provides a method for treating a condition that is treatable by the parent, unmodified therapeutic drug compound (e.g., a cell proliferative disease such as cancer). In the method, a therapeutically effective amount of a compound of the invention is administered to a subject in need thereof.

In one embodiment, the invention provides a method for treating a cell proliferative disease by administering a compound of the invention having a therapeutic drug moiety derived from a therapeutic drug effective in treating cell proliferative disease. Representative cell proliferative diseases treatable by the compounds of the invention include hematologic cancers, such as leukemia, lymphoma, and myeloma; and nonhematologic cancers, such as solid tumor carcinomas (e.g., breast, ovarian, pancreatic, colon, colorectal, non-small cell lung, and bladder), sarcomas, and gliomas.

Therapeutically effective amounts of the compounds will generally range up to the maximally tolerated dosage, but the concentrations are not critical and may vary widely. The precise amounts employed by the attending physician will vary, of course, depending on the compound, route of administration, physical condition of the patient and other factors. The daily dosage may be administered as a single dosage or may be divided into multiple doses for administration.

The amount of the compound actually administered will be a therapeutically effective amount, which term is used herein to denote the amount needed to produce a substantial beneficial effect. Effective doses may be extrapolated from dose-response curves derived from in vitro or animal model test systems. The animal model is also typically used to determine a desirable dosage range and route of administration. Such information can then be used to determine useful doses and routes for administration in humans or other mammals. The determination of an effective dose is well within the capability of those skilled in the art. Thus, the amount actually administered will be dependent upon the individual to which treatment is to be applied, and will preferably be an optimized amount such that the desired effect is achieved without significant side-effects.

Therapeutic efficacy and possible toxicity of the compounds of the invention can be determined by standard pharmaceutical procedures, in cell cultures or experimental animals (e.g., $ED_{50}$, the dose therapeutically effective in 50% of the population; and $LD_{50}$, the dose lethal to 50% of the population). The dose ratio between therapeutic and toxic effects is the therapeutic index, and it can be expressed as the ratio $LD_{50}$ to $ED_{50}$. Modified therapeutic drug compounds that exhibit large therapeutic indices are particularly suitable in the practice of the methods of the invention. The data obtained from cell culture assays and animal studies may be used in formulating a range of dosage for use in humans or other mammals. The dosage of such compounds lies preferably within a range of circulating concentrations that include the $ED_{50}$ with little or no toxicity. The dosage typically varies within this range depending upon the dosage form employed, sensitivity of the patient, and the route of administration. Thus, optimal amounts will vary with the method of administration, and will generally be in accordance with the amounts of conventional medicaments administered in the same or a similar form.

The compounds of the invention can be administered alone, or in combination with one or more additional therapeutic agents. For example, in the treatment of cancer, the compounds can be administered in combination with therapeutic agents including, but not limited to, androgen inhibitors, such as flutamide and luprolide; antiestrogens, such as tomoxifen; antimetabolites and cytotoxic agents, such as daunorubicin, fluorouracil, floxuridine, interferon alpha, methotrexate, plicamycin, mecaptopurine, thioguanine, adriamycin, carmustine, lomustine, cytarabine, cyclophosphamide, doxorubicin, estramustine, altretamine, hydroxyurea, ifosfamide, procarbazine, mutamycin, busulfan, mitoxantrone, carboplatin, cisplatin, streptozocin, bleomycin, dactinomycin, and idamycin; hormones, such as medroxyprogesterone, estramustine, ethinyl estradiol, estradiol, leuprolide, megestrol, octreotide, diethylstilbestrol, chlorotrianisene, etoposide, podophyllotoxin, and goserelin; nitrogen mustard derivatives, such as melphalan, chlorambucil, methlorethamine, and thiotepa, steroids, such as betamethasone; and other antineoplastic agents, such as live *Mycobacterium bovis*, dicarbazine, asparaginase, leucovorin, mitotane, vincristine, vinblastine, and taxotere. Appropriate amounts in each case will vary with the particular agent, and will be either readily known to those skilled in the art or readily determinable by routine experimentation.

Administration of the compounds of the invention is accomplished by any effective route, for example, parenteral, topical, or oral routes. Methods of administration include inhalational, buccal, intramedullary, intravenous, intranasal, intrarectal, intraocular, intraabdominal, intraarterial, intraarticular, intracapsular, intracervical, intracranial, intraductal, intradural, intralesional, intramuscular, intralumbar, intramural, intraocular, intraoperative, intraparietal, intraperitoneal, intrapleural, intrapulmonary, intraspinal, intrathoracic, intratracheal, intratympanic, intrauterine, intravascular, and intraventricular administration, and other conventional means. The compounds of the invention having anti-tumor activity can be injected directly into a tumor, into the vicinity of a tumor, or into a blood vessel that supplies blood to the tumor.

The emulsion, microemulsion, and micelle formulations of the invention can be nebulized using suitable aerosol propellants that are known in the art for pulmonary delivery of the compounds.

The compounds of the invention may be formulated into a composition that additionally comprises suitable pharmaceutically acceptable carriers, including excipients and other compounds that facilitate administration of the compound to a subject. Further details on techniques for formulation and administration may be found in the latest edition of "Remington's Pharmaceutical Sciences" (Maack Publishing Co., Easton, Pa.).

Compositions for oral administration may be formulated using pharmaceutically acceptable carriers well known in the art, in dosages suitable for oral administration. Such carriers enable the compositions containing the compounds of the invention to be formulated as tablets, pills, dragees, capsules, liquids, gels, syrups, slurries, suspensions, suitable for ingestion by a subject. Compositions for oral use may be formulated, for example, in combination with a solid excipient, optionally grinding the resulting mixture, and processing the mixture of granules, after adding suitable additional compounds, if desired, to obtain tablets or dragee cores. Suitable excipients include carbohydrate or protein fillers. These include, but are not limited to, sugars, including lactose, sucrose, mannitol, or sorbitol, starch from corn, wheat, rice, potato, or other plants; cellulose such as methyl cellulose, hydroxypropylmethyl-cellulose, or sodium carboxymethylcellulose; and gums including arabic and tragacanth; as well as proteins, such as gelatin and collagen. If desired, disintegrating or solubilizing agents may be added, such as the crosslinked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage).

Compounds for oral administration may be formulated, for example, as push-fit capsules made of gelatin, as well as soft, sealed capsules made of gelatin and a coating such as glycerol or sorbitol. Push-fit capsules may contain the compounds mixed with filler or binders such as lactose or starches, lubricants such as talc or magnesium stearate, and, optionally, stabilizers. In soft capsules, the covalent conjugates may be dissolved or suspended in suitable liquids, such as fatty oils, liquid paraffin, or liquid polyethylene glycol with or without stabilizers.

For topical or nasal administration, penetrants appropriate to the particular barrier to be permeated are typically used in the formulation. Examples of these are 2-pyrrolidone, N-methyl-2-pyrrolidone, dimethylacetamide, dimethyl-formamide, propylene glycol, methyl or isopropyl alcohol, dimethyl sulfoxide, and azone. Additional agents may further be included to make the formulation cosmetically acceptable. Examples of these are fats, waxes, oils, dyes, fragrances, preservatives, stabilizers, and surface-active agents. Keratolytic agents such as those known in the art may also be included. Examples are salicylic acid and sulfur. For topical administration, the composition may be in the form of a transdermal ointment or patch for systemic delivery of the compound and may be prepared in a conventional manner (see, e.g., Barry, Dermatological Formulations (Drugs and the Pharmaceutical Sciences—Dekker); Harry's Cosmeticology (Leonard Hill Books).

For rectal administration, the compositions may be administered in the form of suppositories or retention enemas. Such compositions may be prepared by mixing the compounds with a suitable non-irritating excipient that is solid at ordinary temperatures but liquid at the rectal temperature and will therefore melt in the rectum to release the drug. Suitable excipients include, but are not limited to, cocoa butter and polyethylene glycols.

The amounts of each of these various types of additives will be readily apparent to those skilled in the art, optimal amounts being the same as in other, known formulations designed for the same type of administration.

Compositions containing the compounds of the invention may be manufactured in a manner similar to that known in the art (e.g., by means of conventional mixing, dissolving, granulating, dragee-making, levigating, emulsifying, encapsulating, entrapping or lyophilizing processes). The compositions may also be modified to provide appropriate release characteristics, sustained release, or targeted release, by conventional means (e.g., coating). As noted above, in one embodiment, the compounds are formulated as an emulsion.

Compositions containing the compounds may be provided as a salt and can be formed with many acids, including but not limited to hydrochloric, sulfuric, acetic, lactic, tartaric, malic, and succinic. Salts tend to be more soluble in aqueous or other protonic solvents than are the corresponding free base forms.

After compositions formulated to contain a compound and an acceptable carrier have been prepared, they can be placed in an appropriate container and labeled for use. Thus, in another aspect, the invention provides kits.

Tocopherol-modified therapeutic drug compounds of the invention are suitable for administration as oil-in-water emulsions and micelle formulations. The compounds provide for high drug loading to enable small volumes for administration.

Emulsions containing tocopherol-modified camptothecin compounds of the invention provide for enhanced stability of the compound's lactone compared to conventional methods of camptothecin administration. Long plasma half-life is achieved for the tocopherol-modified camptothecin compounds resulting in prolonged exposure of a tumor to the compounds. Tocopherol-modified compounds achieve high permeation through lipoidal membranes of tumor cells. Greater anti-tumor response without an increase in toxicity may be provided by the tocopherol-modified camptothecin compounds of the invention as compared to unmodified camptothecin and currently available camptothecin analogs.

Although the compounds of the invention having formula (2) with m=1, formula (3) with n=1, or formula (8) do not include compounds specifically excluded as described above, it will be appreciated that the compositions, emulsion formulations, microemulsion formulations, and micelle formulations include the compounds of the invention having formulae (1)–(8) without such limitation. Methods for administering the compositions, emulsion formulations, microemulsion formulations, and micelle formulations, and methods for treating a condition treatable by administering the compositions, emulsion formulations, microemulsion formulations, and micelle formulations are likewise not limited with regard to the compounds of the invention.

The following examples are provided to illustrate, not limit, the invention.

EXAMPLES

Example 1

The Preparation of a Representative Tocopherol-Modified Camptothecin Compound: Tocopherol Succinate Camptothecin A 500 ml flask was charged with 10.6 grams of d-α-tocopherol succinic acid, 6.97 grams of camptothecin, 6.13 grams of 2-chloro-1-methylpyridinium iodide (CMPI), 5.86 grams of 4-(dimethylamino)pyridine (DMAP), and 200 ml of dry N,N-dimethylacetamide. The mixture was stirred at room temperature for 24 hours, and then heated at 50° C. for 4 hours. The mixture was cooled to room temperature and then was filtered to remove precipitate and the filtrate was collected. To the filtrate were added 250 ml of chloroform and 150 ml of deionized-water to extract the product into the chloroform, and the water fraction was removed using a separation funnel. The chloroform fraction was washed with deionized-water (3×150 ml) in a separation funnel, collected, and dried over anhydrous $MgSO_4$ overnight. The $MgSO_4$ was removed by filtration, and the chloroform was removed with a rotary evaporator under reduced pressure to yield a dark-yellow solid. The product was purified by column chromatography on silica gel. (Yield: 9.50 grams, 55.2%).

$^1$H NMR (300 MHz, $CDCl_3$): δ 8.318 (s, 1H), 8.163–8.135 (d, J=8.4 Hz, 1H), 7.927–7.901(d, J=7.8 Hz, 1H), 7.842–7.787 (m, 1H), 7.682–7.632 (m, 1H), 7.263–7.242 (d, J=6.3 Hz, 1H), 5.702–5.410 (ABq, $J_1$=17.4, $J_2$=70 Hz, 2H), 5.190 (s, 2H), 3.014–2.938 (m, 4H), 2.368–0.809 (m, 54H).

Elemental anal. Calcd. for $C_{53}H_{68}N_2O_8$: C, 73.92; H, 7.96; N, 3.25. Found: C, 73.61; H, 7.90; N, 3.17.

Example 2

The Preparation of a Representative Tocopherol-Modified Camptothecin Compound: Tocopherol Succinate 10-Hydroxycamptothecin Method 1. A 100 ml flask was charged with 1.06 grams of d-α-tocopherol succinic acid, 0.476 grams of thionyl chloride, and 50 ml of toluene. The mixture was stirred at room temperature overnight. The solvent was removed with a rotary evaporator at 50° C., and the residue was collected. To the residue was added 0.728 grams of 10-hydroxycamptothecin and 40 ml of dried tetrahydrofuran with stirring. Then, 0.404 grams of triethylamine in 10 ml of tetrahydrofuran was added dropwise to the reaction mixture. The mixture was stirred at room temperature overnight. The mixture was filtered and white powder was washed with ethyl acetate (3×10 ml). The filtrate was collected. The solvent was removed with a rotary evaporator. The residue was collected, and purified by column chromatography on silica gel with a mobile phase of acetone and chloroform (1:4, v/v). (Yield: 0.85 grams, 48.4%).

MS (Positive ESI): m/z 877 (M)$^+$.

Anal. Calcd. for $C_{53}H_{68}N_2O_9$: C, 72.58; H, 7.81; N, 3.19. Found: C, 72.52; H, 7.84; N, 3.21.

Alternatively, tocopherol succinate 10-hydroxycamptothecin can be prepared as described below.

Method 2. A 100 ml flask was charged with 2.65 grams of d-α-tocopherol succinate, 0.89 grams of thionyl chloride, and 20 ml of toluene. The mixture was stirred at room temperature for 24 hours. The toluene and any excess thionyl chloride were removed with vacuum distillation at 50° C. The remaining residue was dissolved in 15 ml of chloromethane to provide Solution A. To a 100 ml flask, 0.9 grams of 10-hydroxycamptothecin, 0.5 ml of triethylamine, and 25 ml of freshly dried N,N-dimethylacetamide was added with stirring. Then 15 ml of Solution A was slowly added into the mixture through a dropping funnel over 5 minutes. The reaction mixture was stirred at room temperature for 24 hours. The mixture was concentrated by vacuum distillation. 150 ml of ethyl acetate was added to the residue. The mixture was washed with saturated aqueous NaCl solution, (3×100 ml). The mixture was dried over anhydrous $MgSO_4$. The $MgSO_4$ was removed by filtration and the ethyl acetate was then removed by vacuum distillation. The crude product was purified by column chromatography on silica gel. (Yield: 1.14 grams, 52.5%).

Example 3

The Preparation of a Representative Tocopherol-Modified Camptothecin Compound: Tocopherol Succinate 7-Ethyl-10-hydroxycamptothecin Method 1. A 500 ml flask was charged with 22.5 grams of d-α-tocopherol succinate, 7.6 grams of thionyl chloride, and 200 ml of toluene. The mixture was stirred at room temperature for 24 hours. The toluene and the excess thionyl chloride were removed by vacuum distillation. The remaining residue was dissolved in 100 ml of chloromethane to provide Solution A. Solution A was used immediately, and was not exposed to air. To a 500 ml flask, 7.8 grams of 7-ethyl-10-hydroxycamptothecin, 7 ml of triethylamine, and 250 ml of freshly dried N,N-dimethylacetamide was added with stirring. The 100 ml of Solution A was slowly added into the mixture through a dropping funnel over 30 minutes.

The reaction mixture was stirred at room temperature for 24 hours. The solvent was concentrated by vacuum distillation. 500 ml of ethyl acetate was added to the residue. The mixture was washed with saturated aqueous NaCl solution, (3×200 ml). The mixture was dried over anhydrous $MgSO_4$. The $MgSO_4$ was removed by filtration and the ethyl acetate was then removed by vacuum distillation. The crude product was purified by recrystallization with acetone. (Yield: 15.18 grams, 83.9%).

M.P. 171°-173° C.

$^1$H NMR (300 MHz, $CDCl_3$): δ 8.236–8.206 (d, J=9 Hz, 1H), 7.809–7.801 (d, J=2.4 Hz, 1H), 7.648 (s, 1H), 7.572–7.533 (dd, $J_1$=2.7 Hz, $J_2$=9.3 Hz, 1H), 5.781–5.280 (ABq, $J_1$=16.2 Hz, $J_2$=134.0 Hz, 2H), 5.253 (s, 2H), 3.863 (s, 1H), 3.136–3.113 (m, 6H), 2.588 (t, 2H), 2.091 (s, 3H), 2.037 (s, 3H), 1.994 (s, 3H), 1.970–1.852 (m, 2H), 1.821–1.725 (m, 2H), 1.654–0.833 (m, 42H).

MS (Positive ESI): m/z 905 $(M)^+$, 928 $(M+Na)^+$.

Anal. Calcd. for $C_{55}H_{72}N_2O_9$: C, 72.98; H, 8.02; N, 3.09. Found: C, 72.87; H, 8.01; N, 2.88.

Alternatively, the tocopherol succinate 7-ethyl-10-hydroxycamptothecin can be prepared as described below.

Method 2. A 500 ml flask was charged with 8.48 grams of d-α-tocopherol succinate, 3.81 grams of thionyl chloride, and 250 ml of toluene. The mixture was stirred at room temperature overnight. The toluene, and excess thionyl chloride were removed with a rotary evaporator at 50° C., and the residue was collected. To the residue was added 6.27 grams of 7-ethyl-10-hydroxycamptothecin and 250 ml of sodium-dried tetrahydrofuran with stirring. Then, 3.23 grams of triethylamine in 50 ml of tetrahydrofuran was added dropwise to the mixture. The mixture was stirred at room temperature overnight. The mixture was filtered and the white powder was washed with ethyl acetate (3×50 ml). The filtrate was collected. The solvent was removed with a rotary evaporator. The crude product was purified by recrystallization in acetone. (Yield: 8.28 grams, 57.2%).

Example 4

The Preparation of a Representative Tocopherol-Modified Camptothecin Compound: 10,20-Di(tocopherol succinate) 7-Ethyl-10-hydroxycamptothecin A 100 ml flask was charged with 0.905 grams of tocopherol succinate 7-ethyl-10-hydroxycamptothecin, 0.53 grams of d-α-tocopherol succinic acid, 0.255 grams of 2-chloro-1-methylpyridinium iodide, 0.244 grams of 4-(dimethylamino)pyridine and 50 ml of dioxane. The mixture was stirred at room temperature for 24 hours. Thin layer chromatography showed that the reaction was complete. The mixture was filtered to remove the solid phase, and the filtrate was collected. The solvent was removed by vacuum distillation. The crude product was purified by column chromatography on silica gel with 30% ethyl acetate in cyclohexane. (Yield: 0.64 grams, 44.82%).

$^1$H NMR (300 MHz, $CDCl_3$): δ 8.168–8.138 (d, J=9.0 Hz, 1H), 7.813–7.805 (d, J=2.4 Hz, 1H), 7.754–7.536 (dd, $J_1$=2.1 Hz, $J_2$=11.4 Hz, 1H), 7.197 (s, 1H), 5.703–5.409 (ABq, $J_1$=17.4 Hz, $J_2$=71.0 Hz, 2H), 5.243–5.088 (m, 2H), 3.113–2.857 (m, 10H), 2.606–2.564 (t, J=6 Hz, 2H), 2.383–2.184 (m, 2H), 2.090–1.723 (m, 22H), 1.588–0.785 (m, 80H).

MS (Positive ESI): m/z 1418 $(M+H)^+$.

Elemental anal. Calcd. for $C_{88}H_{124}N_2O_{13}$: C, 74.54; H, 8.81; N, 1.98. Found: C, 74.31; H, 8.96; N, 1.75.

$IRv_{max}^{KBr} cm^{-1}$: 2925, 2867, 1751, 1665, 1615, 1657, 1510, 1458, 1413, 1376, 1330, 1218, 1128, 1075, 1060, 1035, 992, 943, 923, 829, 812, 758, 724, 668.

Example 5

The Preparation of a Representative Tocopherol-Modified Camptothecin Compound: Tocopherol-Camptothecin Conjugate with a Hexa(Ethylene Glycol) Linker Preparation of hexa(ethylene glycol) tocopherol succinate. In a 250 ml flask, 2.65 grams of d-α-tocopherol succinic acid and 2.82 grams of hexa(ethylene glycol) was dissolved in 100 ml of toluene with stirring. The toluene was removed with a rotary evaporator (drying by azeotropic distillation). To the mixture was added 100 ml of chloroform, 1.08 grams of N,N-dicyclohexylcarbodiimide, and 100 mg of 4-(dimethylamino)pyridine. The mixture was stirred overnight. Thin layer chromatography with 40% acetone in hexane showed that the reaction was complete. The mixture was washed three times with deionized-water (3×100 ml), and the chloroform fraction was collected, and dried over anhydrous $MgSO_4$ for two hours. After filtration, chloroform was removed by a rotary evaporator. The crude product was purified by column chromatography on silica gel using, successively, the solvents 30% ethyl acetate in hexane, 50% ethyl acetate in hexane, and 30% acetone in hexane. (Yield: 0.53 grams, 13.33%).

Preparation of tocopherol-succinyl-hexa(ethylene glycol) succinic acid. A 100 ml flask was charged with 1.42 grams of hexa(ethylene glycol) tocopherol succinate prepared above, 0.2 grams of succinic acid anhydride, 2 drops of tin (II) ethylhexanoate, and 25 ml of xylene. The mixture was refluxed for 4 hours. After the reaction was complete, the solvent was removed by a rotary evaporator. The crude product was purified by column chromatography on silica gel. (Yield: 0.864 grams, 54%).

Preparation of tocopherol succinate camptothecin with a hexa(ethylene glycol) linker. A 100 ml flask was charged with 0.822 grams of tocopherol-succinyl-hexa(ethylene glycol) succinic acid prepared above, 0.3 grams of camptothecin, 0.47 grams of 2-chloro-1-methylpyridinium iodide, 0.45 grams of 4-(dimethylamino)pyridine, and 40 ml of dried N,N-dimethylacetamide. The reaction mixture was stirred at room temperature overnight. After the reaction was complete, the solvent was removed by vacuum distillation, and the residue was collected. To the residue was added 100 ml of ethyl acetate. After stirring for 30 minutes, the mixture was filtered to remove precipitate, and the filtrate was collected and concentrated. The crude product was purified by column chromatography on silica gel. (Yield: 0.342 grams, 30.4%).

$^1$H NMR (300 MHz, $CDCl_3$): δ 8.388 (s, 1H), 8.240–8.213 (d, J=8.1 Hz, 1H), 7.951–7.923 (d, J=8.4 Hz, 1H), 7.861–7.805 (dt, $J_1$=1.5 Hz, $J_2$=8.4 Hz, 1H), 7.694–7.640 (dt, J=1.2 Hz, $J_2$=8.1 Hz, 1H), 7.269 (s, 1H), 5.708–5.365 (ABq, $J_1$=17.1 Hz, $J_2$=85.8 Hz, 2H), 5.283 (s, 2H), 4.273–4.169 (m, 4H), 3.705–3.673 (t, 2H), 3.631–3.550 (m, 18H), 2.926–2.654 (m, 8H), 2.597–2.552 (t, J=6.9 Hz, 2H), 2.381–2.2.113 (m, 2H), 2.074 (s, 3H), 2.004 (s, 3H), 1.964 (s, 3H), 1.827–1.683 (m, 2H), 1.655 (s, 3H), 1.544–0.964 (m, 24H), 0.875–0.830 (m, 12H).

MS (Positive ESI): m/z 1225 $(M)^+$.

Elemental anal. Calcd. for $C_{88}H_{124}N_2O_{13}$: C, 67.62; H, 7.90; N, 2.29. Found: C, 67.08; H, 8.04; N, 2.07.

IRv$_{max}^{KBr}$cm$^{-1}$: 2925, 2867, 1735, 1667, 1618, 1563, 1500, 1457, 1405, 1366, 1349, 1232, 1204 1141, 1107, 1060, 994, 945, 859, 813, 787, 761, 723, 707.

Example 6

The Preparation of a Representative Tocopherol-Modified Paclitaxel Compound: Tocopherol Succinate Paclitaxel A 250 ml flask was charged with 5.83 grams of tocopherol succinic acid, 2.38 grams of thionyl chloride, and 50 ml of toluene. The mixture was stirred at room temperature overnight. The solvent was removed with a rotary evaporator at 50° C., and the residue was collected. To the residue were added 8.54 grams of paclitaxel and 100 ml of dried tetrahydrofuran with stirring. Then, 1.52 grams of triethylamine in 50 ml of tetrahydrofuran was added dropwise to the reaction mixture. The mixture was stirred at room temperature overnight. The mixture was filtered and the white powder was washed with ethyl acetate (3×10 ml). The filtrate was collected. The solvent was removed with a rotary evaporator. The residue was collected, and purified by recrystallization in acetone and hexane. (Yield: 11.56 grams, 84.6%).

Anal. Calcd. for $C_{80}H_{103}NO_{18}$: C, 70.31; H, 7.59; N, 1.02. Found: C, 70.02, H, 7.83; N, 0.93.

Example 7

The Preparation of a Representative Tocopherol-Modified Docetaxel Compound: Tocopherol Succinate Docetaxel A 250 ml flask is charged with 9.86 grams of d-α-tocopherol succinic acid, 5.0 grams of docetaxel, 3.83 grams of dried N,N-dicyclohexylcarbodiimide, 500 mg of 4-(dimethylamino)pyridine, and 150 ml of chloroform. The mixture is stirred at room temperature overnight. The mixture is filtered to remove precipitate and the filtrate is collected. The solvent is removed with rotary evaporator, and the residue is collected. The crude product is purified by column chromatography on silica gel.

Example 8

The Preparation of Mono-Tocopherol Phthalate

A 100 mL flask was charged with 8.61 grams of dl-α-tocopherol, 2.96 grams of phthalic anhydride, 50 mg of tin (II) 2-ethylhexanoate, and 50 ml of dried N,N-dimethylacetamide. The mixture was stirred at about 140° C. for 24 hours. After the mixture was cooled to room temperature, the mixture was poured into 150 ml of ethyl acetate. The mixture was washed three times with saturated aqueous NaCl (3×100 ml), and dried over anhydrous MgSO$_4$ overnight. The crude product was purified by column chromatography on silica gel with 30% ethyl acetate in hexane. (Yield: 3.6 grams, 31.1%).

$^1$H NMR (300 MHz, CDCl$_3$) δ ppm: 10.80 (bs, 1H), 8.119–8.063 (m, 1H), 7.883–7.828 (m, 1H), 7.678–7.616 (m, 2H), 2.627–2.582 (t, 2H), 2.123 (s, 3H), 2.112 (s, 3H), 2.081 (s, 3H), 1.868–1.702 (m, 2H), 1.616–1.020 (m, 24H), 0.874–0.834 (m, 12H).

Anal. Calcd. for $C_{37}H_{54}O_5$: C, 76.78; H, 9.40. Found: C, 76.57; H, 9.29.

IRv$_{max}^{KBr}$cm$^{-1}$: 3073, 2919, 2858, 1737, 1701, 1578, 1455, 1409, 1373, 1276, 1230, 1107, 1071, 913, 738.

Example 9

The Preparation of Mono-Tocopherol Terephthalate

A 100 mL flask was charged with 4.30 grams of dl-α-tocopherol, 3.32 grams of terephthalic acid, 2.55 grams of 2-chloro-1-methylpyridinium iodide, 0.244 grams of 4-(dimethylamino)pyridine, and 50 ml of dry N,N-dimethylacetamide. The mixture was stirred at 50° C. for 4 hours. Thin layer chromatography showed that the reaction was complete. After the mixture was cooled to room temperature, the mixture was poured into 150 ml of ethyl acetate. The mixture was washed three times with saturated aqueous NaCl (3×100 mL), and dried over anhydrous MgSO$_4$ overnight. The crude product was purified by column chromatography on silica gel with 30% ethyl ether in hexane. (Yield: 1.60 grams, 27.6%)

$^1$H NMR (300 MHz, CDCl$_3$) δ ppm: 11.80 (bs, 1H), 8.374–8.259 (q, $J_1$=8.4 Hz, $J_2$=26.1 Hz, 4H), 2.650–2.607 (t, 2H), 2.130 (s, 3H), 2.066 (s, 3H), 2.024 (s, 3H), 1.895–1.783 (m, 2H), 1.532–1.083 (m, 24H), 0.878–0.839 (m, 12H).

Anal. Calcd. for $C_{37}H_{54}O_5$: C, 76.78; H, 9.40. Found: C, 76.64; H, 9.39.

IRv$_{max}^{KBr}$cm$^{-1}$: 3062, 2924, 2858, 1737, 1696, 1573, 1460, 1424, 1373, 1276, 1240, 1097, 928, 774, 723.

Example 10

The Preparation of a Representative Tocopherol-Modified Camptothecin Compound: Tocopherol Terephthalate Camptothecin A 100 mL flask was charged with 1.16 grams of mono-tocopherol terephthalate prepared above, 0.70 grams of camptothecin, 0.511 grams of 2-chloro-1-methylpyridinium iodide, and 0.489 grams of 4-(dimethylamino)pyridine. The mixture was stirred at 50° C. overnight. Thin layer chromatography showed the reaction was complete. After the mixture cooled to room temperature, the reaction mixture was poured into 150 ml of ethyl acetate. The mixture was filtered and the filtrate was collected. The filtrate was washed with saturated aqueous NaCl (3×100 ml), and dried over anhydrous MgSO$_4$ overnight. The crude product was purified by column chromatography on silica gel. (Yield: 0.560 grams, 30.8%)

$^1$H NMR (300 MHz, CDCl$_3$) δ ppm: 8.387 (s,1H), 8.370–8.242 (q, $J_1$=8.4 Hz, $J_2$=30.3 Hz, 4H), 8.167–8.139 (d, J=8.4 Hz, 1H), 7.937–7.910 (d, J=8.1 Hz, 1H), 7.823–7.774 (t, 1H), 7.672–7.625 (t, 1H), 7.260 (s, 1H), 5.823–5.462 (ABq, $J_1$=17.4 Hz, $J_2$=90.9 Hz, 2H), 5.302 (s, 2H), 2.461 (t, 2H), 2.559–2.312 (m, 2H), 2.123 (s, 3H), 2.056 (s, 3H), 2.015 (s, 3H), 1.844–1.801 (m, 2H), 1.629–1.085 (m, 27H), 0.938–0.789 (m, 12H).

Anal. Calcd. for $C_{57}H_{68}N_2O_8$: C, 75.30; H, 7.54; N, 3.08. Found: C, 74.91; H, 7.56; N, 3.02.

IRv$_{max}^{KBr}$cm$^{-1}$: 3057, 2924, 2858, 1757, 1737, 1675, 1614, 1558, 1450, 1399, 1266, 1235, 1163, 1102, 1020, 723.

Example 11

The Preparation of a Representative Tocopherol-Modified Camptothecin Compound: Tocopherol Cyclohexane-1,2-dicarboxylate 7-Ethyl-10-hydroxycamptothecin Preparation of tocopherol cyclohexane-1,2-dicarboxylic acid. A mixture of 1.54 grams of 1,2-cyclohexanedicarbolic acid anhydride, 8.6 grams of d-α-tocopherol, 1.34 grams of aluminum trichloride, and 100 ml of cyclohexane in a 250 ml flask was heated under reflux for about 30 minutes. After the mixture cooled to room temperature, it was filtered. The filtrate was washed with a dilute aqueous hydrochloric acid solution and then dried over anhydrous $MgSO_4$. The mixture was concentrated, and crude product was purified by column chromatography on silica gel. (Yield: 3.325 grams, 56.9%).

Preparation of tocopherol cyclohexane-1,2-dicarboxylate 7-ethyl-10-hydroxycamptothecin. A mixture of 1.08 grams of tocopherol cyclohexane-1,2-dicarboxylic acid prepared above, 0.44 grams of thionyl chloride, and 20 ml of toluene was stirred under nitrogen overnight. The toluene and excess thionyl chloride were removed by vacuum distillation, and the residue was dissolved in 10 ml of dichloromethane to provide Solution A. In a 100 ml flask, 0.350 grams of SN38 was dissolved in 25 ml of dried N,N-dimethylacetamide to provide Solution B. Solution A and 0.186 g of triethylamine were added to Solution B. The mixture was stirred overnight at room temperature. The crude product was purified by column chromatography on silica gel. (Yield: 0.59 grams, 68.9%).

Example 12

The Preparation of a Representative Tocopherol-Modified Doxorubicin Compound: Tocopherol Succinate Doxorubicin A 100 ml flask is charged with equivalent moles (1 mmole) of tocopherol succinic acid, doxorubicin, and N,N-dicyclohexylcarbodiimide, and 50 ml of dry N,N-dimethylacetamide. The mixture is stirred at room temperature until completion of the reaction. The mixture is filtered to remove white precipitate and the filtrate is collected. The solvent is removed with a rotary evaporator, and the residue is collected. The product is purified by either recrystallization or column chromatography on silica gel.

Example 13

The Preparation of a Representative Tocopherol-Modified Hydroxyzine Compound: Tocopherol Succinate Hydroxyzine A 100 ml flask is charged with equivalent moles (1 mmole) of tocopherol succinic acid, and thionyl chloride, and 50 ml of toluene. The mixture is stirred at room temperature overnight. The solvent is removed with a rotary evaporator at 50° C., and the residue is collected. To the residue are added 1 mmole of hydroxyzine and 40 ml of chloroform with stirring. Then, 1 mmole of triethylamine in 10 ml of chloroform is added dropwise to the reaction mixture at 0–5° C. The mixture is then stirred at room temperature overnight. The mixture is washed with saturated $NaHCO_3$ aqueous solution (3×50 ml). The organic phase is collected, and dried with anhydrous $MgSO_4$. The solvent is removed with a rotary evaporator after removal of $MgSO_4$. The residue is collected, and the crude product is purified by either recrystallization or silica column chromatography.

Example 14

Representative Tocopherol-Modified Therapeutic Drug Compound Solubility

In this example, the solubility of representative tocopherol-modified therapeutic drug compounds of the invention, tocopherol succinate camptothecin and tocopherol succinate 7-ethyl-10-hydroxycamptothecin, was compared to the solubility of camptothecin in a variety of solvents.

The solubility of camptothecin, tocopherol succinate camptothecin, and tocopherol succinate 7-ethyl-10-hydroxycamptothecin was determined in several solvents. Compounds were dissolved in each solvent under constant stirring and temperature to saturation. The resulting solutions were centrifuged and the supernatant was analyzed by high performance liquid chromatography (HPLC).

The comparative solubility (mg/g) of camptothecin, tocopherol succinate camptothecin, and tocopherol succinate 7-ethyl-10-hydroxycamptothecin in various solvents is shown in Table 1.

TABLE 1

Solubility Comparison of Camptothecin and Tocopherol Succinate Camptothecins.

| Solvent | Camptothecin (mg/g) | VESA-SN38[1] (mg/g) | VESA-CPT[2] (mg/g) | Temperature (° C.) |
|---|---|---|---|---|
| PEG-400 NF | — | 0.017 | 17.5 | Room Temp. |
| TPGS | — | 27.6 | >133.3 | 65 |
| Vitamin E USP/NF | 1.96 | 398.2 | >288.3 | 65 |
| Soybean Oil USP | 0.00 | 3.3 | 45.2 | Room Temp. |
| Captex 300 EP | — | 4.4 | 96.7 | Room Temp. |
| Tween 80 NF | — | 2.7 | 48.3 | 65 → Room Temp. |
| Ethanol Denatured | — | 4.2 | 57.1 | Room Temp. |
| Methanol | — | 3.8 | 14.4 | Room Temp. |
| Acetonitrile | 0.09 | 3.1 | 49.6 | Room Temp. |
| Chloroform | 0.71 | >97.0 | >372.5 | Room Temp. |
| DMSO | 50 | 30.5 | >255.5 | Room Temp. |
| Methylene dichloride | 0.9 | >99.7 | >336.5 | Room Temp. |
| Propylene Glycol, USP | — | 3.2 | 0.4633 | Room Temp. |
| Glycerin USP/EP/BP/JP | — | 2.8 | 2.541 | Room Temp. |

[1]VESA-SN38: tocopherol succinate 7-ethyl-10-hydroxycamptothecin
[2]VESA-CPT: tocopherol succinate camptothecin The results in Table 1 illustrate that tocopherol succinate camptothecin and tocopherol succinate 7-ethyl-10-hydroxycamptothecin both have substantial solubility in oils, and have particularly high solubility in vitamin E (α-tocopherol).

Example 15

Representative Tocopherol-Modified Therapeutic Drug Compound-Containing Emulsions In this example, representative emulsions containing tocopherol-modified therapeutic drug compounds of the invention are described.

A. Tocopherol Succinate 7-Ethyl-10-Hydroxycamptothecin Emulsion

Tocopherol succinate 7-ethyl-10-hydroxycamptothecin, prepared as described in Example 3, was dissolved in vitamin E and then emulsified with the use of a microfluidizer (M110Y Microfluidics) in the presence of d-α-tocopherol polyethylene glycol 1000 succinate (TPGS), Poloxamer 407, and saline to produce an emulsion having the following composition (% by weight):

| | |
|---|---|
| Tocopherol succinate-7-ethyl-10-hydroxycamptothecin | 0.69% |
| Vitamin E | 7.31% |
| TPGS | 5% |
| Poloxamer 407 | 1% |
| Saline | 86% |

The emulsion was filtered through a 0.2 µm filter and vialed in sterile glass vials. Mean particle size was approximately 50 nM as determined by submicron particle sizer (Nicomp Model 370), with 99% of the particles less than 80 nm. No evidence of precipitation or loss of concentration as measured by HPLC was observed for at least 3 months when stored at 4° C.

B. Tocopherol Succinate 7-Ethyl-10-hydroxycamptothecin Emulsion

Tocopherol succinate 7-ethyl-10-hydroxycamptothecin, prepared as described in Example 3, was dissolved in vitamin E and then emulsified with the use of a microfluidizer (M110Y Microfluidics) in the presence of TPGS and saline to produce an emulsion having the following composition (% by weight):

| | |
|---|---|
| Tocopherol succinate-7-ethyl-10-hydroxycamptothecin | 0.69% |
| Vitamin E | 7.31% |
| TPGS | 5% |
| Saline | 87% |

This formulation resulted in a more yellow and thicker emulsion than the emulsion prepared as described above that included Poloxamer 407. The emulsion was filtered through a 0.2 µm filter and vialed in sterile glass vials. Mean particle size was approximately 75 nm as determined by submicron particle sizer (Nicomp Model 370), with 99% of the particles less than 170 nm. No evidence of precipitation or loss of concentration as measured by HPLC was observed for at least 3 months when stored at 4° C.

C. Tocopherol Succinate Camptothecin Emulsion

Tocopherol succinate camptothecin, prepared as described in Example 1, was dissolved in vitamin E and then emulsified with the use of a microfluidizer (M110Y Microfluidics) in the presence of TPGS, Poloxamer 407, and saline to produce an emulsion having the following composition (% by weight):

| | |
|---|---|
| Tocopherol succinate camptothecin | 0.74% |
| Vitamin E | 7.26% |
| TPGS | 5% |
| Poloxamer 407 | 1% |
| Saline | 86% |

The emulsion was filtered through a 0.2 µm filter and vialed in sterile glass vials. Mean particle size was approximately 40 nm as determined by submicron particle sizer (Nicomp Model 370), with 99% of the particles less than 75 nm. No evidence of precipitation or loss of concentration as measured by HPLC was observed for at least 3 months when stored at 4° C.

D. Tocopherol Succinate Camptothecin Emulsion

Tocopherol succinate camptothecin, prepared as described in Example 1, was dissolved in vitamin E and then emulsified with the use of a microfluidizer (M110Y Microfluidics) in the presence of TPGS, Poloxamer 407, and saline to produce an emulsion having the following composition (% by weight):

| | |
|---|---|
| Tocopherol succinate camptothecin | 1.48% |
| Vitamin E | 6.52% |
| TPGS | 5% |
| Poloxamer 407 | 1% |
| Saline | 86% |

The emulsion was filtered through a 0.2 µm filter and vialed in sterile glass vials. Mean particle size was approximately 30 nm as determined by submicron particle sizer (Nicomp Model 370), with 99% of the particles less than 100 nm. No evidence of precipitation or loss of concentration as measured by HPLC was observed for at least 3 months when stored at 4° C.

E. Tocopherol Succinate 7-Ethyl-10-hydroxycamptothecin Emulsion

Tocopherol succinate 7-ethyl-10-hydroxycamptothecin, prepared as described in Example 3, was dissolved in vitamin E and then emulsified with the use of a microfluidizer (M110Y Microfluidics) in the presence of TPGS and citric acid buffered saline to produce an emulsion having the following composition (% by weight):

| | |
|---|---|
| Tocopherol succinate-7-ethyl-10-hydroxycamptothecin | 0.69% |
| Vitamin E | 7.31% |
| TPGS | 5% |
| Citric acid buffered saline, pH 3.0 | 87% |

The emulsion was filtered through a 0.2 µm filter and vialed in sterile glass vials. Mean particle size was approximately 60 nm as determined by submicron particle sizer (Nicomp Model 370), with 99% of the particles less than 150 nm. No evidence of precipitation or loss of concentration as measured by HPLC was observed for at least 3 months when stored at 4° C. and 25° C.

F. Tocopherol Succinate 7-Ethyl-10-hydroxycamptothecin Emulsion

Tocopherol succinate 7-ethyl-10-hydroxycamptothecin, prepared as described in Example 3, was dissolved in vitamin E and then emulsified with the use of a microfluidizer (M110Y Microfluidics) in the presence of TPGS and succinate buffered saline to produce emulsions having the following composition (% by weight):

Formulation 1

| | |
|---|---|
| Tocopherol succinate-7-ethyl-10-hydroxycamptothecin | 0.69% |
| Vitamin E | 7.31% |
| TPGS | 5% |
| Succinate buffered saline, pH 4.0 | 87% |

The emulsion was filtered through a 0.2 µm filter and vialed in sterile glass vials. Mean particle size was approximately 70 nm as determined by submicron particle sizer (Nicomp Model 370), with 99% of the particles less than 170 nm. No evidence of precipitation or loss of concentration as measured by HPLC was observed for at least 3 months when stored at 4° C. and 25° C.

Formulation 2

| Tocopherol succinate-7-ethyl-10-hydroxycamptothecin | 1% |
|---|---|
| Vitamin E | 7% |
| TPGS | 5% |
| Succinate buffered saline, pH 4.0 | 87% |

The emulsion was filtered through a 0.2 μm filter and vialed in sterile glass vials. Mean particle size was approximately 70 nm as determined by submicron particle sizer (Nicomp Model 370), with 99% of the particles less than 170 nm. No evidence of precipitation or loss of concentration as measured by HPLC was observed for at least 1 month when stored at 4° C., 25° C., and 40° C.

Formulation 3

| Tocopherol succinate-7-ethyl-10-hydroxycamptothecin | 1% |
|---|---|
| Vitamin E | 6% |
| TPGS | 4% |
| Succinate buffered saline, pH 4.0 | 89% |

The emulsion was filtered through a 0.2 μm filter and vialed in sterile glass vials. Mean particle size was approximately 95 nm as determined by submicron particle sizer (Nicomp Model 370), with 99% of the particles less than 220 nm. No evidence of precipitation or loss of concentration as measured by HPLC was observed for at least 1 month when stored at 4° C., 25° C., and 40° C.

G. Tocopherol Succinate 7-Ethyl-10-hydroxycamptothecin (VESA-SN38) Micelle Formulation Tocopherol succinate 7-ethyl-10-hydroxycamptothecin was dissolved in a mixture containing TPGS, PEG(300), and ethanol at about 50° C.—about 60° C. with stirring for about 1 hour to form a transparent solution. To this solution was added either deionized-water (DI-water), Poloxamer 407 and DI-water, Poloxamer 188 and DI-water, or 0.9% NaCl aqueous solution to form Formulations 1–5 respectively below. The formulations were stirred for a few minutes to form transparent micelle solutions having the following compositions (% by weight):

Formulation 1

| VESA-SN38 | 0.2% |
|---|---|
| TPGS | 5% |
| Ethanol | 5% |
| PEG(300) | 5% |
| DI-water | 84.8% |

The formulation solution was filtered through a 0.2 μm filter and vialed in sterile glass vials. No evidence of precipitation or loss of concentration as measured by HPLC was observed for at least 11 weeks when stored at 4° C.

Formulation 2

| VESA-SN38 | 0.2% |
|---|---|
| TPGS | 5% |
| Poloxamer 407 | 1.7% |
| Ethanol | 5% |
| PEG(300) | 5% |
| DI-water | 83.1% |

The formulation solution was filtered through a 0.2 μm filter and vialed in sterile glass vials. No evidence of precipitation or loss of concentration as measured by HPLC was observed for at least 11 weeks when stored at 4° C.

Formulation 3

| VESA-SN38 | 0.2% |
|---|---|
| TPGS | 5% |
| PEG(300) | 5% |
| Ethanol | 5% |
| Poloxamer 188 | 1.7% |
| DI-water | 83.1% |

The formulation solution was filtered through a 0.2 μm filter and vialed in sterile glass vials. No evidence of precipitation or loss of concentration as measured by HPLC was observed for at least 11 weeks when stored at 4° C., and 25° C.

Formulation 4

| VESA-SN38 | 0.2% |
|---|---|
| TPGS | 2% |
| PEG(300) | 2% |
| Ethanol | 4% |
| Saline | 91.8% |

The formulation solution was filtered through a 0.2 μm filter and vialed in sterile glass vials. No evidence of precipitation or loss of concentration as measured by HPLC was observed for at least 1 week when stored at 4° C., 25° C., or 40° C.

Formulation 5

| VESA-SN38 | 0.5% |
|---|---|
| TPGS | 5% |
| PEG(300) | 5% |
| Ethanol | 10% |
| Saline | 79.5% |

The formulation solution was filtered through a 0.2 μm filter and vialed in sterile glass vials. No evidence of precipitation or loss of concentration as measured by HPLC was observed for at least 3 weeks when stored at 4° C.

H. Tocopherol Succinate 7-Ethyl-10-hydroxycamptothecin (VESA-SN38) Micelle Formulation Tocopherol succinate 7-ethyl-10-hydroxycamptothecin was dissolved in a mixture containing TPGS, PEG(300), and ethanol at about 50° C.—about 60° C. with stirring for about 1 hour to form a transparent solution. To this solution was added succinate buffered saline to form Formulations 1 and 2 below. The formulations were stirred for a few minutes to form transparent micelle solutions having the following compositions (% by weight):

Formulation 1

| | |
|---|---|
| VESA-SN38 | 0.2% |
| TPGS | 2% |
| Ethanol | 4% |
| PEG(300) | 2% |
| Succinate buffered saline, pH 4.0 | 91.8% |

The formulation solution was filtered through a 0.2 μm filter and vialed in sterile glass vials.

Formulation 2

| | |
|---|---|
| VESA-SN38 | 0.5% |
| TPGS | 5% |
| Ethanol | 10% |
| PEG(300) | 5% |
| Succinate buffered saline, pH 4.0 | 79.5% |

The formulation solution was filtered through a 0.2 μm filter and vialed in sterile glass vials.

Example 16

In Vitro Stability of Lactone of Representative Tocopherol-Modified Therapeutic Drug Compounds in Presence of Human Albumin In this example, the in vitro stability in the presence of human albumin of the lactone form of representative tocopherol-modified therapeutic drug compounds of the invention, tocopherol succinate camptothecin and tocopherol succinate 7-ethyl-10-hydroxycamptothecin, was compared to the in vitro stability of the lactone form of camptothecin.

Because the lactone (ring E) is a critical moiety for camptothecin activity and it is reported not to be stable under physiological conditions (pH=7.4), the stability of the lactone for tocopherol succinate camptothecin and tocopherol succinate 7-ethyl-10-hydroxycamptothecin was determined. The solubilization of tocopherol succinate camptothecin and tocopherol succinate 7-ethyl-10-hydroxycamptothecin in the oil-phase is thought to protect the lactone from hydrolysis and thus provide improved lactone stability in physiological conditions. To evaluate lactone stability, a saline buffered solution (10 mM, pH 7.4) containing 4% human serum albumin was incubated at 37° C. in the presence of camptothecin (dissolved in DMSO), tocopherol succinate camptothecin emulsion (prepared as described in Example 15C, referred to herein as "SN2300 emulsion") or tocopherol succinate 7-ethyl-10-hydroxycamptothecin emulsion (prepared as described in Example 15A, referred to herein as "SN2310 emulsion"). High performance liquid chromatography with fluorescence detection was used to analyze the decrease in the concentration of the lactone form over time.

Figure 12:
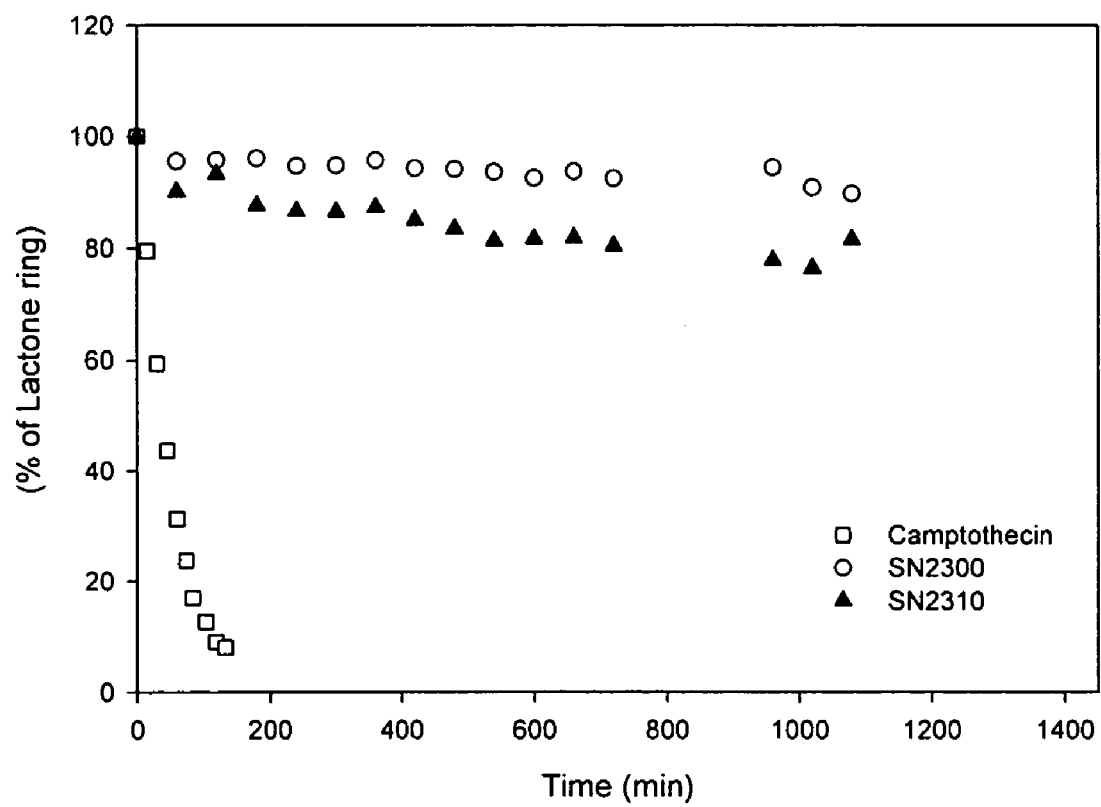
FIG. 12 is a graph comparing the in vitro stability of the lactone form of camptothecin and of two representative tocopherol-modified therapeutic drug compounds of the invention (SN2300, tocopherol succinate camptothecin; and SN2310, tocopherol succinate 7-ethyl-10-hydroxycamptothecin)

FIG. 12 illustrates the percent change in concentration of the lactone form over time for camptothecin, tocopherol succinate camptothecin (SN2300), and tocopherol succinate 7-ethyl-10-hydroxycamptothecin (SN2310), in the presence of human serum albumin. The stability of the lactone of tocopherol succinate camptothecin and tocopherol succinate 7-ethyl-10-hydroxycamptothecin is greater than that of camptothecin. This dramatic increase in the stability of the lactone may result in increased activity compared to the unmodified camptothecin parent compound.

Example 17

In Vitro Cytotoxicity of Representative Tocopherol-Modified Therapeutic Drug Compounds In this example, the in vitro cytotoxicty of representative tocopherol-modified therapeutic drug compounds of the invention, tocopherol succinate camptothecin and tocopherol succinate 7-ethyl-10-hydroxycamptothecin, was compared to the in vitro cytotoxicity of camptothecin, 10-hydroxycamptothecin, SN38, irinotecan, and topotecan.

The in vitro cytotoxicity, as measured by $GI_{50}$ (50% of growth inhibition) values, of tocopherol succinate camptothecin and tocopherol succinate 7-ethyl-10-hydroxycamptothecin was investigated and compared to the National Cancer Institute (NCI) $GI_{50}$ values for camptothecin, 10-hydroxycamptothecin, SN-38, irinotecan, and topotecan in the following cancer cell lines: NCI-H460 (ATCC #HTB-177) (non-small cell lung), HCT-15 (ATCC #CCL-225) (colorectal), HT-116 (ATCC #CCL-247) (colorectal), HT-29 (ATCC #HTB-38) (colorectal), MCF-7 (ATCC #HTB-22) (breast), and OVCAR-3 (ATCC #HTB-161) (ovarian).

The study was performed using emulsion formulations of tocopherol succinate 7-ethyl-10-hydroxycamptothecin (described in Example 15A) and tocopherol succinate camptothecin (described in Example 15C) diluted in the corresponding cell media. The cells were in contact with varying concentrations of the test article for a period of 48 hours. At the end of 48 hours, staining with ALAMAR BLUE was performed to determine the number of viable cells and calculate the degree of cellular growth inhibition as compared to a control group. The percent of inhibition versus concentration was fit to the Hill equation to determine concentration that produces 50% of growth inhibition ($GI_{50}$).

Figure 13:
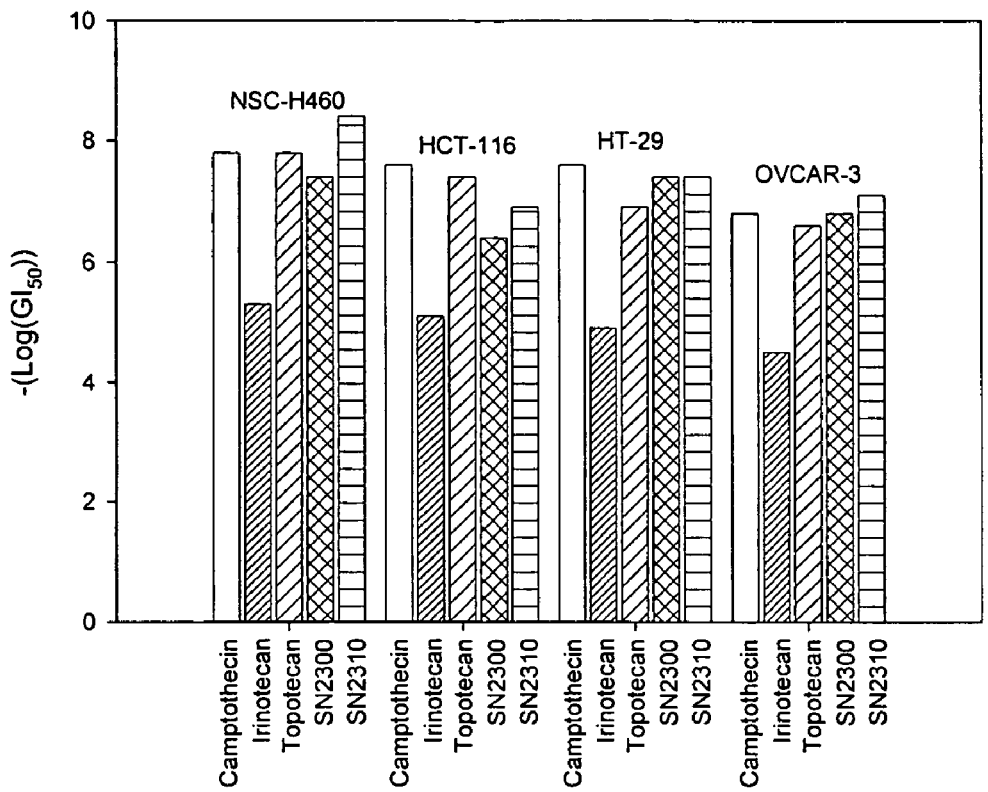
FIG. 13 is a graph comparing GI$_{50}$ values reported by NCI for camptothecin, irinotecan hydrochloride (irinotecan), and topotecan hydrochloride (topotecan) with GI$_{50}$ values obtained for two representative tocopherol-modified therapeutic drug compounds of the invention (SN2300 and SN2310) for cell lines: H460, HCT-116, HT29, and OVCAR-3.

The sensitivity of the tested cell lines to tocopherol succinate camptothecin (SN2300), tocopherol succinate 7-ethyl-10-hydroxycamptothecin (SN2310), camptothecin, irinotecan, and topotecan is illustrated in Table 2 and FIG. 13.

TABLE 2

Comparative drug concentration that produce 50% cell growth inhibition ($GI_{50}$).

| Cell line | CPT (NCI) | 10-HO-CPT (NCI) | SN38 (NCI) | Irinotecan (NCI) | Topotecan (NCI) | VESA-CPT | VESA-SN38 |
|---|---|---|---|---|---|---|---|
| NCI-H460 (NSCLC) | 16 nM | 11 nM | 1.4 nM | 5.01 μM | 19.9 nM | 43 nM | 4 nM |
| HCT-15 (COLON) | 160 nM | 356 nM | 7.9 nM | 31.6 μM | 501 nM | 20 μM | 99 nM |

TABLE 2-continued

Comparative drug concentration that produce 50% cell growth inhibition ($GI_{50}$).

| Cell line | CPT (NCI) | 10-HO-CPT (NCI) | SN38 (NCI) | Irinotecan (NCI) | Topotecan (NCI) | VESA-CPT | VESA-SN38 |
|---|---|---|---|---|---|---|---|
| OVCAR-3 (OVARIAN) | 160 nM | 62 nM | 2.9 nM | 31.6 µM | 251 nM | Poor activity | 83 nM |
| HCT-116 (COLON) | 40 nM | 27 nM | 21 nM | 7.9 µM | 39.8 nM | 449 nM | 119 nM |
| HT29 (COLON) | 126 nM | 112 nM | 1 nM | 12.58 µM | 125 nM | 434 nM | 91 nM |
| MCF-7 (BREAST) | 13 nM | 10 nM | | 3.98 µM | 15.8 nM | 325 nM | |

CPT: Camptothecin;
10-HO-CPT: 10-hydroxycamptothecin;
SN38: 7-ethyl-10-hydroxycamtothecin;
VESA-CPT: tocopherol succinate camptothecin;
VESA-SN38: tocopherol succinate 7-ethyl-10-hydroxycamothecin.

The results in Table 2 illustrates that formulations of tocopherol-modified therapeutic drug compounds of the invention provide effective anti-tumor activity.

FIG. 13 is a plot of the $GI_{50}$ values (concentration that produces 50% growth inhibition) determined for tocopherol succinate camptothecin and tocopherol succinate 7-ethyl-10-hydroxycamptothecin in four of the tested cell lines. The values reported by the NCI in these same cancer cell lines for camptothecin, irinotecan, and topotecan is also included as comparison. A high $GI_{50}$ value corresponds to a low drug concentration to produce 50% inhibition. From the graph, it is clear that the compounds of the invention, tocopherol succinate camptothecin and tocopherol succinate 7-ethyl-10-hydroxycamptothecin, show a high level of cytotoxic activity similar to camptothecin.

Example 18

Pharmacokinetics of Representative Tocopherol-Modified Therapeutic Drug Compounds In this example, the pharmacokinetics of representative tocopherol-modified therapeutic drug compounds of the invention, tocopherol succinate camptothecin and tocopherol succinate 7-ethyl-10-hydroxycamptothecin, was compared to camptothecin, irinotecan, and topotecan.

The pharmacokinetic profiles of tocopherol succinate camptothecin and tocopherol succinate 7-ethyl-10-hydroxycamptothecin were investigated in Sprague-Dawley rats following a bolus, intravenous administration of emulsion formulations of the drug compounds (SN2300 emulsion and SN2310 emulsion) via the lateral tail vein at a dose of approximately 14 mg of drug compound/kg of body weight. Blood samples were collected for up to 120 hours post dose via the jugular vein. The concentration of each camptothecin derivative in plasma was determined by high performance liquid chromatography (HPLC) with fluorescence detection. A noncompartmental analysis was carried out using Win-Nonlin (v 4.1).

Figure 14A:
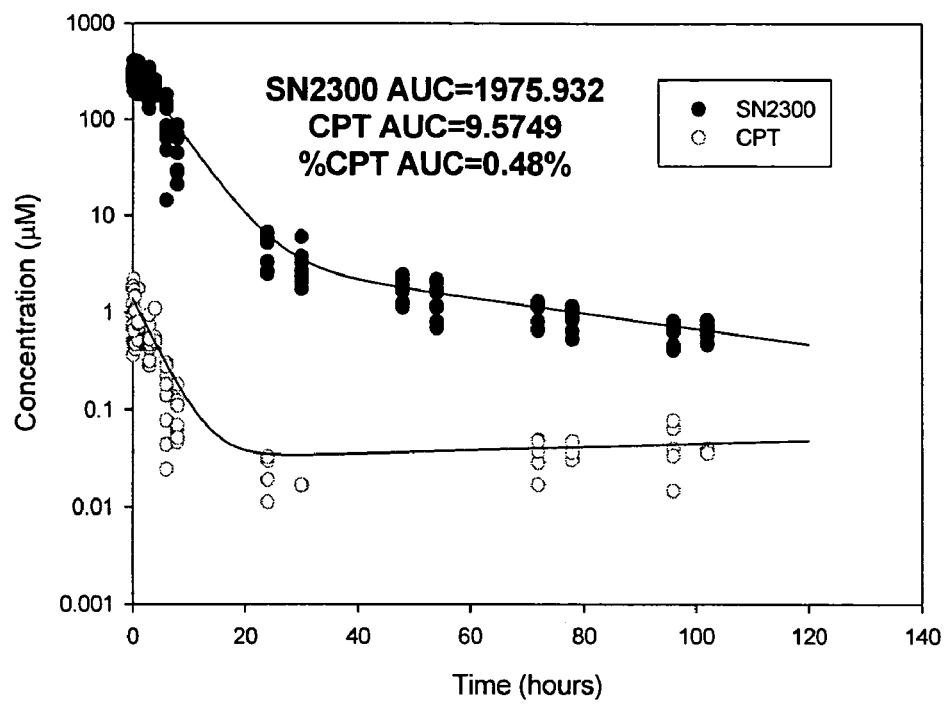
FIGS. 14A and 14B are graphs of concentration-time values after intravenous injection of 13.8 mg/kg of two representative tocopherol-modified therapeutic drug compounds of the invention (FIG. 14A, SN2300.
Figure 14B:
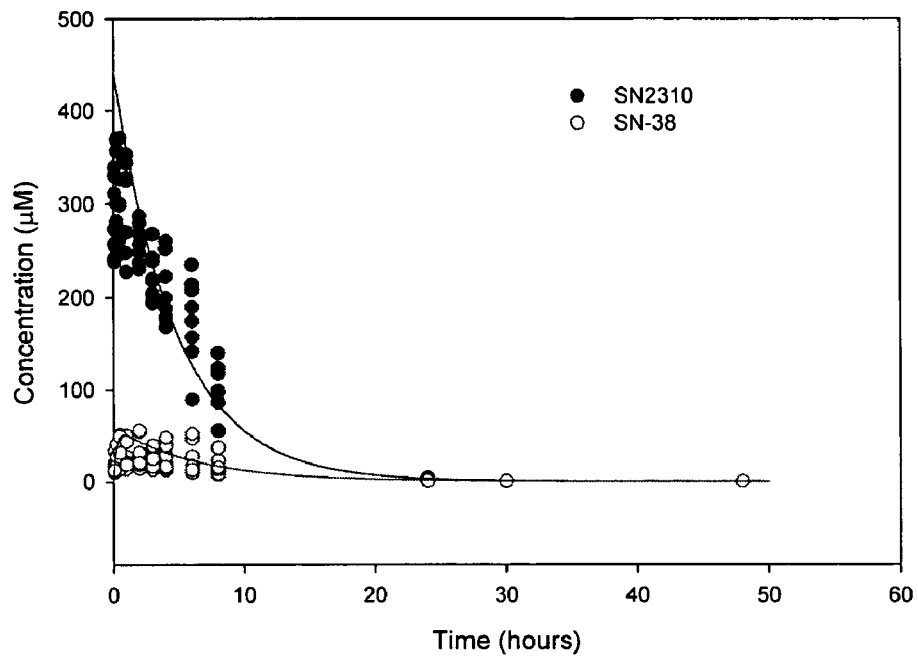

The pharmacokinetic profiles of tocopherol succinate camptothecin (SN2300) and tocopherol succinate 7-ethyl-10-hydroxycamptothecin (SN2310) are illustrated in FIGS. 14A and 14B, respectively. FIGS. 14A and 14B illustrate concentration-time values after an intravenous injection of 13.8 mg of drug compound/kg of body weight for tocopherol succinate camptothecin (SN2300 emulsion) and tocopherol succinate 7-ethyl-10-hydroxycamptothecin (SN2310 emulsion), respectively. Referring to FIGS. 14A and 14B, a prolonged plasma half-life following intravenous administration, particularly for tocopherol succinate camptothecin, is shown.

The calculated plasma elimination half-life, mean residence time, and clearance of tocopherol succinate camptothecin (SN2300), tocopherol succinate 7-ethyl-10-hydroxycamptothecin (SN2310), camptothecin, irinotecan, and topotecan is provided in Table 3.

The term "plasma elimination half-life" refers to the time necessary to reduce the drug concentration in plasma by 50% after equilibrium is reached. The term "elimination rate constant" refers to the fraction of drug eliminated per unit of time. With first-order elimination, the rate of elimination is directly proportional to the serum drug concentration. There is a linear relationship between rate of elimination and serum drug concentration. Although the amount of drug eliminated in a first-order process changes with concentration, the fraction of a drug eliminated remains constant.

The term "clearance" refers to a measure of the body's ability to eliminate drug and is a hypothetical volume of distribution of drug which is cleared per unit time (i.e., mL/min) by any pathway of drug removal. It is important to clarify that the clearance does not indicate how much drug is being removed, rather, the volume of biological fluid such as blood or plasma that would have to be completely freed of drug to account for the elimination. The term "volume of distribution" refers to a calculated volume of body fluid that would be required to dissolve the total amount of drug at the same concentration as that found in the blood. It is a proportionality constant relating the amount of drug in the body to the measured concentration in biological fluid (blood, plasma, serum).

TABLE 3

Comparative pharmacokinetic parameters following intravenous administration in rats of tocopherol succinate camptothecin (SN2300) and tocopherol succinate 7-ethyl-10-hydroxycamptothecin (SN2310) compared to camptothecin, irinotecan, and topotecan.

| Compound | $t_{1/2}$ (hr) (elimination) | MRT (hours) | Clearance (l/hr/kg) |
|---|---|---|---|
| SN2300 | 29.08 | 9.40 | 0.0081 |
| SN2310 | 3.49 | 5.15 | 0.0067 |
| Camptothecin[a] | 1.7 | — | 8.81 |

TABLE 3-continued

Comparative pharmacokinetic parameters following intravenous administration in rats of tocopherol succinate camptothecin (SN2300) and tocopherol succinate 7-ethyl-10-hydroxycamptothecin (SN2310) compared to camptothecin, irinotecan, and topotecan.

| Compound | $t_{1/2}$ (hr) (elimination) | MRT (hours) | Clearance (l/hr/kg) |
|---|---|---|---|
| Topotecan[a] | 1.06 | — | 3.22 |
| Irinotecan[b] | 1.54 | 1.43 | 2.22 |

[a]El-Gizawy SA, Hedaya MA. Cancer Chemother. Pharmacol., 43: 364–370 (1999).
[b]Atsumi R, Okazaji O Hakusui H. Biol. Pharm. Bull., 18 (8): 1114–1119 (1995).

Table 3 illustrates that the calculated plasma elimination half-life of tocopherol succinate camptothecin (SN2300) and tocopherol succinate 7-ethyl-10-hydroxycamptothecin (SN2310) is approximately 30-times and 3-times longer than the commercially available analogs, respectively. The higher mean residence time (MRT) and lower clearance rate suggest a longer tumor exposure time to these new derivatives, which may indicate a potential for increased chemotherapeutic effect.

Through lipophilic modification of therapeutic drug compounds, the plasma elimination half-life of the parent therapeutic drug compound can be increased. The compounds of the invention, by virtue of the lipophilic moiety (e.g., tocopherol moiety), have increased plasma elimination half-life compared to the parent therapeutic drug. As illustrated above for tocopherol succinate camptothecin and tocopherol succinate 7-ethyl-10-hydroxycamptothecin, the plasma elimination half-life is significantly increased compared to the parent compounds.

Example 19

In Vivo Anti-Tumor Activity of Representative Tocopherol-Modified Therapeutic Drug Compounds in Human Tumor Xenographs In this example, the in vivo anti-tumor activity of representative tocopherol-modified therapeutic drug compounds of the invention, tocopherol succinate camptothecin and tocopherol succinate 7-ethyl-10-hydroxycamptothecin, was compared to the anti-tumor effect of irinotecan.

NCI-H460 Human Tumor Xenograft. Athymic mice were subcutaneously implanted with a cell suspension ($10^7$ cells/mouse). When tumors reached an appropriate size, animals were randomized into groups of eight and intravenously administered the following compounds at a dose of 15 mg of drug compound/kg of body weight on a schedule of q1 dx5 for two consecutive weeks:
Saline-control group
Irinotecan
SN2300 emulsion
SN2310 emulsion
HT-29 Human Tumor Xenograft. Athymic mice were subcutaneously implanted with 30–40 mg tumor fragments using 12-gauge trocar needles. A sufficient number of mice were implanted with fragments so tumors in narrow weight range (100–200 mg) were selected for the trial on staging day (SD). The animals selected with tumors in the proper size range were randomized into six groups of 10 animals and intravenously administered the following test compounds:

Saline-control group (q1dx5 for 2 weeks)
Irinotecan (15 mg/kg, q1dx5 for 2 weeks)
SN2300 emulsion (15 mg/kg, q1dx5 for 2 weeks)
SN2310 emulsion (15 mg/kg, q1dx5 for 2 weeks)
SN2300 emulsion (15 mg/kg, q3dx10)
SN2310 emulsion (15 mg/kg, q3dx10)

In both xenograph studies, animal body weights and tumors were measured twice weekly following the initiation of dosing. The tumor measurements were performed using a caliper (millimeters); the tumor volume was calculated based on the formula: $(\text{Length} \times \text{width}^2)/2 = \text{Volume (mm}^3)$.

Figure 15A:
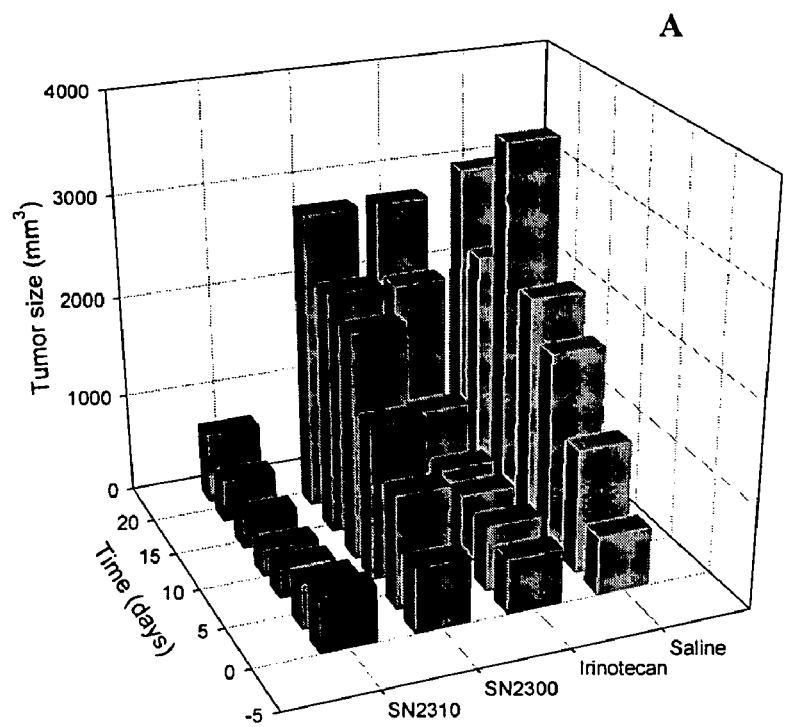
FIGS. 15A and 15B are graphs illustrating tumor growth (mm$^3$) over time in xenographs treated with saline, irinotecan, and two representative tocopherol-modified therapeutic drug compounds of the invention (SN2300 and SN2310) in two different tumor models (FIG. 15A, NCI-H460.
Figure 15B:
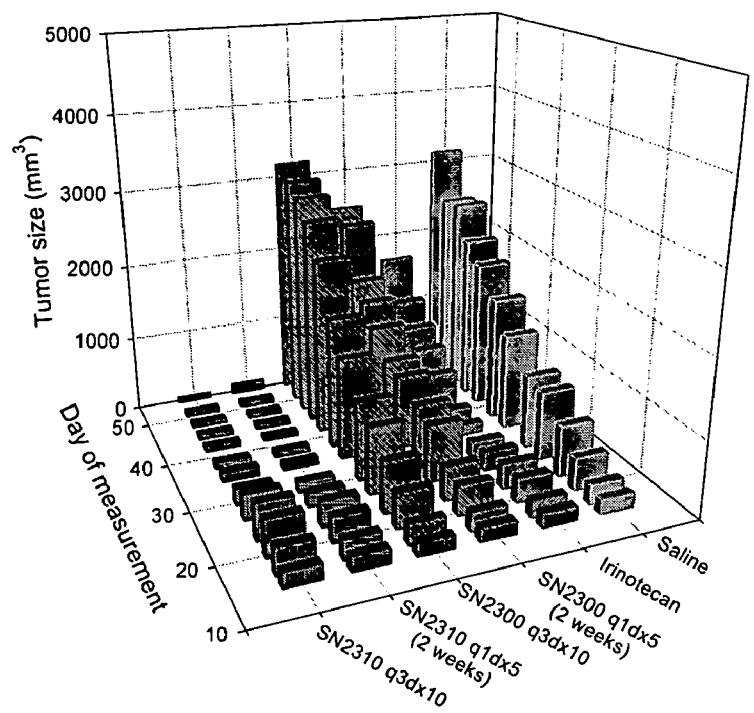

The anti-tumor effect of SN2300 and SN2310 emulsions administered to athymic mice implanted with NCI-H460 human tumor cells and HT-29 human tumor cells is graphically represented in FIGS. 15A and 15B, respectively. Although the SN2300 emulsion showed little to no anti-tumor effect in this model, the SN2310 emulsion exhibited substantial anti-tumor effect as compared to both saline control and irinotecan.

The calculated tumor response parameters for the HT-29 xenograft study is provided in Table 4. Fifty-five days after dose initiation, 30% of mice in the control group were sacrificed because of tumor size (>4000 mm³) and the median tumor size was 3136 mm³. At this same timepoint, 80% of the mice in the SN2310 (q3dx10) group presented no measurable tumor. In addition, the SN2310 (q1dx5) group had a median tumor size of 126 mm³ with 40% having no measurable tumor. At the same time, the irinotecan group showed a median tumor size of 1637 mm³. The results indicate that the administration of SN2310 produces significant anti-tumor activity.

TABLE 4

Calculated Tumor Response Parameters from the HT-29 Xenograft Study.

| Group | Schedule | Tumor Growth Delay (T − C) (days) | Tumor Growth Inhibition (% T/C) | Number of animals with no measurable tumor on Day 55 |
|---|---|---|---|---|
| Saline | q1dx5 (2 weeks) | — | — | 0/10 |
| Irinotecan | q1dx5 (2 weeks) | 14 | 52 | 0/10 |
| SN2300 | q1dx5 (2 weeks) | 8.5 | 79 | 0/10 |
| SN2300 | q3dx10 | 0 | 102 | 0/10 |
| SN2310 | q1dx5 (2 weeks) | >28* | 4 | 4/10 |
| SN2310 | q3dx10 | >28* | 2 | 8/10 |

*90% of tumors in this group had still not reached maximum pre-determined size.
T − C = Median Time for Treatment group (T) and Control group (C) to reach a predetermined size.
% T/C = (Treated median tumor weight)/(Control median tumor weight) × 100 (at Day 55).

While the preferred embodiment of the invention has been illustrated and described, it will be appreciated that various changes can be made therein without departing from the spirit and scope of the invention.

The invention claimed is:

1. Butanedioic acid, (2R)-3,4-dihydro-2,5,7,8-tetramethyl-2-[(4R,8R)-4,8,12-trimethyltridecyl]-2H- 1-benzopyran-6-yl (4S)-4-ethyl-3,4,12,14-tetrahydro-3,14-dioxo-1H-pyrano[3′,4′:6,7]indolizino[1,2-b]quinolin-4-yl ester.

2. Butanedioic acid, (2R)-3,4-dihydro-2,5,7,8-tetramethyl-2-[(4R, 8R)-4,8,12-trimethyltridecyl]-2H-1-benzopyran-6-yl (4S)-4-ethyl-3,4,12,14-tetrahydro-4-hydroxy-3,14-dioxo-1H-pyrano[3',4':6,7]indolizino]1,2-b]quinolin-9-yl ester.

3. Butanedioic acid, (4S)-4,11-diethyl -3,4,12,14-tetrahydro-4-hydroxy-3,14-dioxo- 1H-pyranof[3',4':6,7]indolizino[1,2-b]quinolin-9-yl (2R)-3,4-dihydro-2,5,7,8-tetramethyl-2 [(4R,8R)-4,8,12-trimethyltridecyl]-2H-1-benzopyran-6-yl ester.

4. A pharmaceutical composition, comprising a pharmaceutically acceptable carrier and the compound of claim 1, wherein the compound is in an amount from about 0.005 to about 3.0 weight percent based on the total weight of the composition.

5. A pharmaceutical composition, comprising a pharmaceutically acceptable carrier and the compound of claim 2, wherein the compound is in an amount from about 0.005 to about 3.0 weight percent based on the total weight of the composition.

6. A pharmaceutical composition, comprising a pharmaceutically acceptable carrier and the compound of claim 3, wherein the compound is in an amount from about 0.005 to about 3.0 weight percent based on the total weight of the composition.

7. A method for treating a solid tumor carcinoma, comprising administering to a subject in need thereof a therapeutically effective amount of compound of claim 1.

8. A method for treating a solid tumor carcinoma, comprising administering to a subject in need thereof a therapeutically effective amount of the compound of claim 2.

9. A method for treating a solid tumor carcinoma, comprising administering to a subject in need thereof a therapeutically effective amount of the compound of claim 3.

10. A method for treating a solid tumor carcinoma, comprising administering to a subject in need thereof an emulsion comprising:
    (a) an oil phase comprising
        (i) the compound of claim 1 and
        (ii) a lipophilic medium; and
    (b) an aqueous phase.

11. A method for treating a solid tumor carcinoma, comprising administering to a subject in need thereof an emulsion comprising:
    (a) an oil phase comprising
        (i) the compound of claim 2; and
        (ii) a lipophilic medium; and
    (b) an aqueous phase.

12. A method for treating a solid tumor carcinoma, comprising administering to a subject in need thereof an emulsion comprising:
    (a) an oil phase comprising
        (i) the compound of claim 3; and
        (ii) a lipophilic medium; and
    (b) an aqueous phase.

13. The method of any of claims 7–12, wherein the solid tumor carcinoma is selected from breast, ovarian, pancreatic, colon, colorectal, non-small cell lung, and bladder carcinomas.

14. The method of any of claims 10–12, wherein the lipophilic medium comprises a tocopherol.

* * * * *

UNITED STATES PATENT AND TRADEMARK OFFICE
CERTIFICATE OF CORRECTION

| | |
|---|---|
| PATENT NO. | : 7,223,770 B2 |
| APPLICATION NO. | : 10/978222 |
| DATED | : May 29, 2007 |
| INVENTOR(S) | : Y. Zhang |

Page 1 of 1

It is certified that error appears in the above-identified patent and that said Letters Patent is hereby corrected as shown below:

| COLUMN | LINE | | |
|---|---|---|---|
| (12) Pg. 1, col. 1 | Inventors | | "Zhang et al." should read --Zhang-- |
| (75) Pg. 1, col. 1 | Inventors | | "Inventors: Yuehua Zhang, Mill Creek, WA (US); Lynn C. Gold, Seattle, WA (US)" should read --Inventor: Yuehua Zhang, Mill Creek, WA (US)-- |
| (56) Pg. 1, col. 2 | Refs. Cited (Other Publs., Item 8) | | "<http://www/" should read --<http://www.-- |
| 40 (Claim 1, line 4) | 65 | | "indolizinol" should read --indolizino-- |
| 41 (Claim 2, line 4) | 2 | | "]1,2-b]" should read --[1,2-b]-- |
| 41 (Claim 3, line 2) | 5 | | "14-dioxo- 1H-pyranof" should read --14-dioxo-1H-pyrano-- |
| 41 (Claim 7, line 3) | 56 | | after "amount of" insert --the-- |

Signed and Sealed this

Twenty-third Day of October, 2007

JON W. DUDAS
*Director of the United States Patent and Trademark Office*